US012714837B2

(12) United States Patent
Masri et al.

(10) Patent No.: US 12,714,837 B2
(45) Date of Patent: Aug. 25, 2026

(54) COMPOSITIONS AND DELIVERY METHODS FOR TREATING DENTAL INFECTIONS, INFLAMMATION, SENSITIVITY, AND FOR USE IN DENTAL RESTORATIONS

(71) Applicants: UNIVERSITY OF MARYLAND, BALTIMORE, Baltimore, MD (US); UNIVERSITY OF MARYLAND, COLLEGE PARK, College Park, MD (US)

(72) Inventors: Radi Masri, Ellicott City, MD (US); Didier Depireux, Ellicott City, MD (US)

(73) Assignees: UNIVERSITY OF MARYLAND, BALTIMORE, Baltimore, MD (US); UNIVERSITY OF MARYLAND, COLLEGE PARK, College Park, MD (US)

( * ) Notice: Subject to any disclaimer, the term of this patent is extended or adjusted under 35 U.S.C. 154(b) by 389 days.

(21) Appl. No.: 17/174,055

(22) Filed: Feb. 11, 2021

(65) Prior Publication Data

US 2021/0252263 A1 Aug. 19, 2021

Related U.S. Application Data

(62) Division of application No. 15/324,724, filed as application No. PCT/US2015/039559 on Jul. 8, 2015, now Pat. No. 10,960,192.

(Continued)

(51) Int. Cl.

*A61M 37/00* (2006.01)
*A61C 5/50* (2017.01)

(Continued)

(52) U.S. Cl.

CPC ............... *A61M 37/00* (2013.01); *A61C 5/50* (2017.02); *A61C 19/06* (2013.01); *A61C 19/063* (2013.01);

(Continued)

(58) Field of Classification Search

CPC ....... A61M 37/00; A61M 19/00; A61N 2/008; A61N 2/02; A61N 2/06; A61C 5/50;

(Continued)

(56) References Cited

U.S. PATENT DOCUMENTS 5,295,832 A * 3/1994 Evans .................... A61C 17/02 433/216
6,315,709 B1 11/2001 Garibaldi (Continued)

FOREIGN PATENT DOCUMENTS

EP 1841314 B1 3/2014
WO 9856302 A1 12/1998

(Continued)

OTHER PUBLICATIONS

Ballal, Microleakage of Composite Resin Restorations, Australian Dental Association, 53:369-370 (2008).

(Continued)

*Primary Examiner* — Nicholas D Lucchesi
(74) *Attorney, Agent, or Firm* — Nevrivy Patent Law Group P.L.L.C.

(57) ABSTRACT

The present invention provides a method of treating a condition affecting a tooth or periodontium in a subject, comprising administering to the subject's tooth or periodontium a composition comprising biocompatible magnetic, magnetizable, or magnetically responsive agents; and applying an external magnetic field, wherein the magnetic, magnetizable, or magnetically responsive agents migrate to a desired location in response to the externally applied mag- (Continued)

netic field, thereby treating a condition affecting the tooth or periodontium in the subject.

9 Claims, 13 Drawing Sheets

Related U.S. Application Data

(60) Provisional application No. 62/021,890, filed on Jul. 8, 2014.

(51) Int. Cl.
*A61C 19/06* (2006.01)
*A61C 19/08* (2006.01)
*A61K 9/00* (2006.01)
*A61K 9/50* (2006.01)
*A61K 31/155* (2006.01)
*A61K 41/00* (2020.01)
*A61K 47/69* (2017.01)
*A61M 19/00* (2006.01)
*A61N 2/00* (2006.01)
*A61N 2/02* (2006.01)
*A61N 2/06* (2006.01)

(52) U.S. Cl.
CPC ............ *A61C 19/08* (2013.01); *A61K 9/0063* (2013.01); *A61K 9/5094* (2013.01); *A61K 31/155* (2013.01); *A61K 41/00* (2013.01); *A61K 47/6923* (2017.08); *A61K 47/6929* (2017.08); *A61M 19/00* (2013.01); *A61N 2/008* (2013.01); *A61N 2/02* (2013.01); *A61N 2/06* (2013.01); *A61M 2037/0007* (2013.01); *A61M 2210/0637* (2013.01)

(58) Field of Classification Search
CPC ....... A61C 19/06; A61C 19/063; A61C 19/08; A61K 31/105; A61K 41/00; A61K 47/6929; A61K 47/6923
See application file for complete search history.

(56) References Cited

U.S. PATENT DOCUMENTS 6,652,778 B1* 11/2003 Twarowski ........... G02F 1/0147 252/582
6,997,863 B2* 2/2006 Handy ................... A61N 1/406 977/904
7,189,198 B2 3/2007 Harburn
7,833,016 B2* 11/2010 Gharib ..................... A61C 5/62 433/81
8,316,862 B2 11/2012 Shapiro
8,544,474 B2* 10/2013 Sandhu ................ A61K 9/5094 128/897
8,651,113 B2* 2/2014 Seeney ................ A61K 9/5094 128/899
8,715,150 B2* 5/2014 Creighton ................. A61P 9/10 977/773
9,421,173 B2* 8/2016 Benita .................. A61K 9/1272
9,883,878 B2* 2/2018 Creighton .......... A61B 17/3207
10,576,295 B2* 3/2020 Shapiro .................. A61N 2/004
10,688,292 B2* 6/2020 Shapiro ................. A61M 37/00
10,960,192 B2 3/2021 Masri
2004/0101809 A1* 5/2004 Weiss ..................... A61C 19/06 433/32
2005/0129727 A1 6/2005 Weber
2005/0271732 A1 12/2005 Seeney
2006/0041182 A1 2/2006 Forbes
2006/0228421 A1 10/2006 Seeney
2007/0275353 A1* 11/2007 Gharib .................... A61L 27/04 433/224
2008/0255498 A1 10/2008 Houle
2009/0287036 A1 11/2009 Shapiro
2010/0272776 A1* 10/2010 Harlow ................... A61L 27/38 424/93.1
2013/0040267 A1* 2/2013 Bergheim .............. A61C 17/20 433/226
2013/0129634 A1* 5/2013 Tampieri ................ C01B 25/45 424/400
2013/0137063 A1 5/2013 Edwards
2014/0073835 A1* 3/2014 Shapiro .................. A61N 2/004 600/9
2015/0044628 A1* 2/2015 Flyash ................ A61C 19/066 433/32
2019/0118265 A1* 4/2019 Nie .................... A61K 47/6923

FOREIGN PATENT DOCUMENTS

WO 2007139809 A2 12/2007
WO 2014066786 A1 5/2014

OTHER PUBLICATIONS

Cheng et al., Prevention of acute graft-versus-host disease by magnetic nanoparticles of Fe3O4 combined with cyclosporin A in murine models, Int J Nanomedicine, 6:2183-2189 (2011).
Gilliam et al., Iontophoresis in the Treatment of Cervical Dentinal Sensitivity—A Review, J West Soc Periodontol Abstr, 38:129-133 (1990).
Goldstein, The Longevity of Direct and Indirect Posterior Restorations is Uncertain and may be Affected by a Number of Dentist-, Patient-, and Material-Related Factors, J Evid Based Dent Pract, 10:30-31 (2010).
Hellstern et al., Systemic Distribution and Elimination of Plain and with Cy3.5 Functionalized Poly(vinyl alcohol) Coated Superparamagnetic Maghemite Nanoparticles After Intraarticular Injection in Sheep In Vivo, J Nanosci Nanotechnol, 6:3261-3268 (2006).
Ikeda et al., Facilitatory effect of AC-iontophoresis of lidocaine hydrochloride on the permeability of human enamel and dentine in extracted teeth, Arch Oral Biol, 58:341-347 (2013).
Jiang et al., The reversal effect of magnetic Fe3O4 nanoparticles loaded with cisplatin on SKOV3/DDP ovarian carcinoma cells, Int J Nanomedicine, 4:107-114 (2009).
Jain et al., Biodistribution, Clearance, and Biocompatibility of Iron Oxide Magnetic Nanoparticles in Rats Mol Pharm, 5:316-327 (2008).
Lubbe et al., Clinical Experiences with Magnetic Drug Targeting: A Phase | Study with 4'-Epidoxorubicin in 14 Patients with Advanced Solid Tumors, Cancer Res, 56:4686-4693 (1996).
Lubbe et al., Clinical Applications of Magnetic Drug Targeting, J Surg Res, 95:200-206 (2001).
Li et al., Measurement of the full-field polymerization shrinkage and depth of cure of dental composites using digital mage correlation, Dental Materials, 25:582-588 (2009).
Lynch et al., Guidance on posterior resin composites: Academy of Operative Dentistry—European Section, Journal of Dentistry, 42:377-383 (2014).
Marcenes et al., Global Burden of Oral Conditions in 1990-2010: A Systematic Analysis, J Dent Res, 2:592-597 (2013).
Mjor, the Density and Branching of Dentinal Tubules in Human Teeth, Archs oral Biol, 41:401-412 (1996).
Molday et al., Immunospecific Ferromagnetic Iron-Dextran Reagents for the Labeling and magnetic Separation of Cells, Journal of Immunological Methods, 52:353-367 (1982).
Malhotra es al., Resin-Based Composite as a Direct Esthetic Restorative Material, Compend Contin Edu Dent, 33:14-24 (2011).
Drummond, Degradation, fatigue and failure of resin dental composite materials, J Dent Res, 87:710-719 (2008).
Tiefenauer et al., Antibody-Magnetite Nanoparticles: In Vitro Characterization of a Potential Tumor-Specific Contrast Agent for Magnetic Resonance Imaging, Bioconjugate Chem., 4:347-352 (1993).

(56) References Cited

OTHER PUBLICATIONS

Liu et al., Preparation and Characterization of Superparamagnetic Functional Polymeric Microparticles, China Particuology, 1:76-79 (2003).
Shiau, Dentin Hypersensitivity, J Evid Base Dent Pract, 12:220-228 (2012).
Masri et al., Magnetic Delivery of Therapeutic Nanoparticles to the Dental Pulp, National Institutes of Health, Grantome (http://grantome.com/grant/NIH/R21-DE024227-01 accessed on May 28, 2015), p. 1-2.
Xu et al., Site-directed research of magnetic nanoparticles in magnetic drug targeting, Journal of Magnetism and Magnetic Materials, 293:514-519 (2005).
Turi et al., Sub-Micrometric Liposomes as Drug Delivery Systems in the Treatment and Periodontitis, International Journal of Immunopathology and Pharmacology, 25:657-670 (2012).
Extended European Search Report form European Appl. No. 15819202.1, mailed on Apr. 26, 2018.
European Communication from Appl. No. 15819202.1, mailed on Apr. 22, 2020.
Office Action from U.S. Appl. No. 15/324,724, mailed on Oct. 5, 2018.
Office Action from U.S. Appl. No. 15/324,724, mailed on Jul. 23, 2020.
Office Action from U.S. Appl. No. 15/324,724, mailed on Dec. 30, 2019.
Office Action from U.S. Appl. No. 15/324,724, mailed on May 2, 2019.

* cited by examiner

FIG. 9

Inside mouth

Cheek tongue

COMPOSITIONS AND DELIVERY METHODS FOR TREATING DENTAL INFECTIONS, INFLAMMATION, SENSITIVITY, AND FOR USE IN DENTAL RESTORATIONS

CROSS REFERENCE TO RELATED APPLICATIONS

This application claims the benefit of U.S. provisional application No. 62/021,890, filed Jul. 8, 2014, which is incorporated herein by reference in its entirety.

STATEMENT OF FEDERALLY SPONSORED RESEARCH AND DEVELOPMENT

This invention was made with government support under Grant No. DE024227 awarded by National Institutes of Health. The government has certain rights in the invention.

FIELD OF THE INVENTION

This invention generally relates to the field of dentistry. In particular, this invention relates to biocompatible magnetic, magnetizable, or magnetically responsive agent compositions and magnetic based delivery methods for treating conditions affecting a tooth or periodontium such as tooth infections, tooth sensitivity, pulpitis and for use in restorative dentistry applications.

BACKGROUND OF THE INVENTION

Dental caries (tooth decay) is a costly global health problem that affects billions of individuals worldwide. Marcenes et al., *J Dent Res.* 2013; 92 (7):592-597. It is the most prevalent chronic disease on the planet. According to the World Health Organization (WHO), 60-90% of school children and nearly 100% of adults have tooth decay. WHO. Oral Health. Media Centre, Fact Sheets. 2012; N°318.

In its early stages, dental decay is characterized by localized demineralization of the outer layer of the tooth (enamel, FIG. 1A). This demineralization, caused by the by-products of bacterial metabolism (e.g.: lactic acid, ammonia, urea, indole), spreads over time and affects deeper structural layers of the tooth (dentin) and results in cavity formation. In addition to bacterial by-product induced demineralization of tooth structure, bacterial antigens (e.g.: lipopolysaccharides, lipoteichoic acid) diffuse through dentin and elicit immune responses that result in pulpal inflammation (pulpitis) and pain. These immune responses involve the activation of the innate immune system and the release of inflammatory mediators (e.g.: prostaglandin E2 (PGE2), bradykinin, CGRP) and proinflammatory cytokines (e.g.: tumor necrosis factor-alpha (TNF-$\alpha$), interleukin-1 alpha (IL-1$\alpha$), and IL-1$\beta$).

These agents will cause inflammation of the dental pulp, or pulpitis, which is a common, painful, and costly global public health problem that affects the quality of life of patients. Pulpitis is characterized by sharp, shooting pain, evoked by thermal stimuli (reversible pulpitis) or debilitating, dull, throbbing pain that occurs spontaneously or can be evoked by mechanical or thermal stimuli and lingers after cessation of the stimulus, necessitating emergency care (irreversible pulpitis). The quality and severity of the pain correlates with the extent of irritation from bacteria and other etiologies. Diagnosis can be complicated because the pain can be referred to other orofacial structures, or to adjacent teeth.

Reversible pulpitis is treated by removing affected tooth structures, primarily enamel and dentin (FIG. 1A). The pulp chamber is typically left intact, and the resulting defect repaired using a filling material. This longstanding form of treatment is aimed at reducing repeated insults to the pulp by providing insulation from thermal changes and metabolic by-products of bacterial fermentation, and by providing protection from chewing forces. However, filling materials do not provide full protection. Tooth decay and the resulting pulpal inflammation are not self-limiting, and in many cases the disease progresses to irreversible pulpitis. Irreversible pulpitis is more difficult to treat. Unless the pulp is exposed due to large carious lesions, topical drug administration is challenging because the pulp is encased in hard tissues (dentin and enamel). To date, the only acceptable therapy is to perform a root canal treatment, which involves a radical amputation of the tooth pulp. Root canal treatment can be painful, morbid, and costly. It necessitates the removal of a significant amount of tooth structure, weakening the tooth, especially in molars.

Unfortunately, available strategies for the treatment of pulpitis are limited, aggressive and outdated. They are focused on excising the affected hard tissues (cavity preparation) and the placement of a filling if the patient is suffering from reversible pulpitis or the radical amputation of the tooth pulp if the patient is suffering from irreversible pulpitis. Available systemic pharmacologic treatments are focused on controlling symptoms of pulpitis but do not reverse the pathology. Topical drug administration is typically not feasible until the disease has reached an advanced stage, when large carious lesions are present and the pulp is exposed.

Tooth sensitivity is also an important dental problem. Approximately 40-80% of the population suffers from tooth sensitivity. The sensitivity can be characterized by momentary, sharp-shooting pain arising from exposed dentin in response to various stimuli, such as thermal, mechanical, osmotic or chemical elements. It is commonly referred to as dentinal sensitivity or dentinal hypersensitivity. Dentinal sensitivity occurs primarily due to exposed dentinal tubules and the presence of thin and porous enamel. Several methods to treat this condition exist, ranging from the use of topical fluoride, the application of specialized dentifrices and the application of desensitizing agents.

Dentinal tubules are microscopic channels that extend outwards, through dentin, from the pulp to the enamel border. In humans, they are 0.3-2 μm in diameter and usually taper and may exhibit branching as they approach the pulp. Dentinal tubules are abundant in dentin and their density ranges from 10-30 tubules per 100 $\mu m^2$ of dentin and their density and branching increases as they approach the pulp. Mjor et al., *Arch Oral Biol.* 1996; 41 (5):401-412. Dentinal tubules serve as an important route for the delivery of nutrients to the dentin from the pulp and contain: dentinal fluids, un-mineralized collagen, cellular processes of odontoblasts-cells that line the roof of the pulp chamber and deposit dentin, sensory nerve terminals and immunoglobulins and complement proteins that assist with the defense against microorganisms. It is thought that mechanical and thermal stimuli activate sensory processes in dentinal tubules by changing the pressure and the movement of the fluid in these tubules. It is also through these tubules that the by-products of bacterial fermentation and bacterial antigens attack the pulp and cause pulpitis. Dentists recognized the importance of these tubules decades ago and they routinely use them to provide microretention to bond fillings to tooth structure. Dentists have tried iontophoresis to propel charged minerals including potassium and fluoride to block these tubules to reduce tooth sensitivity with limited success. Gillam et al., *J West Soc Periodontol Periodontal Abstr.* 1990; 38 (4):129-133; Ikeda et al., *Arch Oral Biol.* 2013; 58 (4):341-347.

Periodontal diseases, such as gingivitis and periodontitis, can lead to tooth loss if left untreated. Treatments often require visits to a dental office. Periodontal disease is mainly the result of infections and inflammation of the gums and bone that surround and support the teeth. Periodontal disease can be challenging to treat, particularly where infections reside in hard to reach areas of the periodontium.

Accordingly, there is a need in the art to provide improved compositions and methods for treating conditions affecting the teeth or periodontium, such as pulpitis, dentinal sensitivity, decay, gingivitis and periodontitis.

SUMMARY OF THE INVENTION

It is to be understood that both the foregoing general description of the embodiments and the following detailed description are exemplary, and thus do not restrict the scope of the embodiments.

The invention is based on the surprising discovery that magnets can be used to effectively and efficiently deliver magnetic, magnetizable, or magnetically responsive agents such as nanoparticles to desired locations in the tooth or periodontium. In some embodiments, the invention exploits dentinal tubules to deliver nanoparticles or nanoparticles loaded with medications or restorative/bonding agents and uses magnetic forces to transport the nanoparticles to the dentinal tubules and/or the pulp (FIG. 2). Unlike diffusion, which is a passive process, magnetic forces can be arranged to act in one direction; and they can actively transport substantially more nanoparticles or drug loaded nanoparticles to a target than diffusion or iontophoresis. In some embodiments, this gentle and active delivery can obviate the need for root canal treatment and can be less expensive, and less painful and traumatic than root canal treatment. It can allow for intervention at an earlier stage of the disease, such as before pulp necrosis.

In one embodiment, the invention provides a method of treating a condition affecting a tooth or periodontium in a subject, comprising i) administering to the subject's tooth or periodontium a composition comprising biocompatible magnetic, magnetizable, or magnetically responsive agents; and
ii) applying an external magnetic field wherein the magnetic, magnetizable, or magnetically responsive agents migrate to a desired location in response to the externally applied magnetic field, thereby treating a condition affecting the tooth or periodontium in the subject.

In another embodiment, the invention provides a composition for treating a condition affecting a tooth or periodontium in a subject comprising biocompatible magnetic, magnetizable, or magnetically responsive agents and an effective amount of a therapeutic agent, wherein the therapeutic agent is selected from the group consisting of a remineralizing agent, a restorative/bonding material, an anti-inflammatory agent, an immunosuppressant, an analgesic, an antibody, an antibiotic, an antibacterial, an anti-fungal, a dental anesthetic, a desensitizing agent, recombinant RNA, recombinant DNA, lipopolysaccharides, a therapeutic protein, and combinations thereof.

In another embodiment, the invention provides a dental delivery system for delivering one or more therapeutically effective agents to a desired location in a subject's tooth or periodontium comprising i) one or more magnets capable of applying an external magnetic field; and
ii) a composition comprising biocompatible magnetic, magnetizable, or magnetically responsive agents; wherein the magnetic, magnetizable, or magnetically responsive agents migrate to a desired location in response to the externally applied magnetic field.

In some embodiments, the compositions and methods can be used to deliver or guide several types of FDA approved medications (e.g., steroids, local anesthetics, antibiotics, fluorides, and bonding agents) through dentinal tubules and as such can be used for a wide range of dental conditions including pulpal pain, pulpal infection and inflammation, and tooth sensitivity. They can also be used to improve bond strength of dental restorations. In some embodiments, the magnetic, magnetizable, or magnetically responsive agents are nanoparticles comprising biodegradable iron cores coated by starch or chitosan, which in turn can be coated with therapeutic agents such as, e.g.: prednisolone, ofloxacin, lidocaine, or fluoride. These particles have been tested extensively and determined to be biocompatible and non-toxic in preclinical models (Hellstern et al., *J. Nanosci Nanotechnol.* 2006; 6 (9-10):3261-3268; Jain et al., *Mol Pharm.* 2008; 5 (2):316-327) and in human clinical trials (Lubbe et al., *Cancer Res.* 1996; 56 (20):4686-4693; Lubbe et al., *J Surg Res.* 2001; 95 (2):200-206.), and have been used to treat inner and middle ear diseases (Komanee et al., Putting Therapeutic Nanoparticles Where They Need To Go By Magnet Systems Design and Control. *Magnetic Drug Targeting.* 2012).

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 9. One embodiment of a magnet configuration for delivering agents to the lower teeth is shown. For the lower teeth, a single magnet or multiple magnets can be employed and placed in parallel, under the mandible, right under the tooth to be treated. The magnet can be placed inside a holder to keep its position fixed with respect to the base of the mandible.

DETAILED DESCRIPTION

Figure 1:
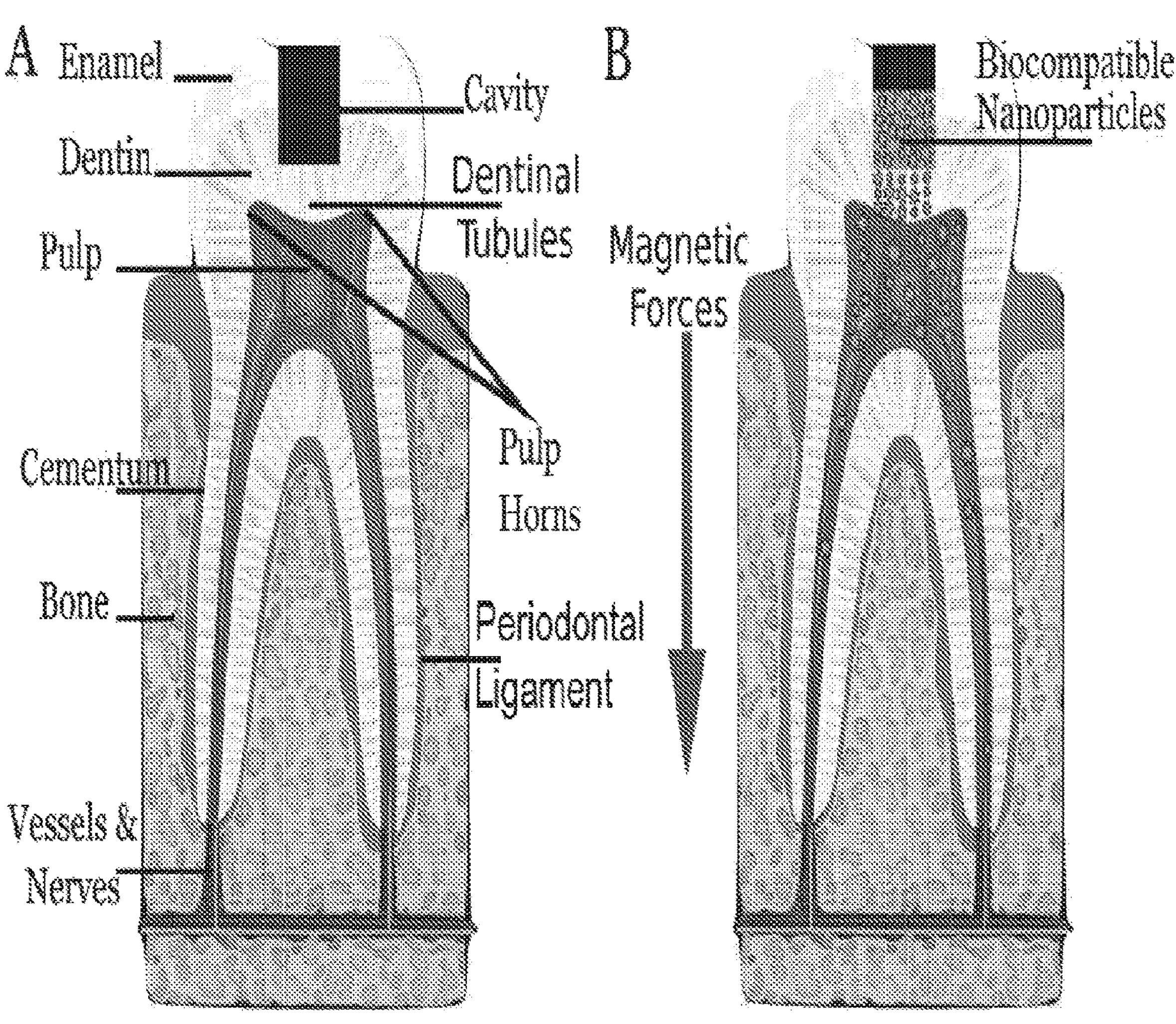
FIG. 1. (A) Tooth anatomy and (B) experimental design.

The invention is based on the surprising discovery that magnets can be used to effectively and efficiently deliver nanoparticles to tissues in the tooth. In some aspects, the present invention provides a new technique to deliver therapeutic agents to the pulp without affecting the integrity of the pulp chamber. In some embodiments, the invention takes advantage of naturally occurring dentinal tubules and use magnetic forces to direct biocompatible therapeutic magnetic particles into the tooth pulp (FIG. 1B). These dentinal tubules extend outwards, through dentin, from the pulp to the enamel border. The tubules are 0.3-2 μm in diameter and are abundantly present in dentin (10-30 tubules per 100 $\mu m^2$ of dentin). Experiments described herein demonstrate, among other things, efficient delivery of 100-300 nm prednisolone-eluting nanoparticles in therapeutic concentrations to the pulp chamber of human teeth, using magnet arrays.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting the specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

I. Systems and Methods

In one embodiment, the invention provides a method of treating a condition affecting a tooth or periodontium in a subject, comprising i) administering to the subject's tooth or periodontium a composition comprising biocompatible magnetic, magnetizable, or magnetically responsive agents; and ii) applying an external magnetic field wherein the magnetic, magnetizable, or magnetically responsive agents migrate to a desired location in response to the externally applied magnetic field, thereby treating a condition affecting the tooth or periodontium in the subject.

As used herein, the terms "treatment," "treating," and the like, refer to obtaining a desired effect, such as a desired pharmacologic, physiologic effect and/or cosmetic effect. The effect can be prophylactic in terms of completely or partially preventing a disease or symptom thereof and/or can be therapeutic in terms of a partial or complete cure for a disease and/or adverse effect attributable to the disease or condition.

The subject to be treated is not limiting. In some embodiments the subject is a mammal, such as a human, monkey, chimpanzee, gorilla, pig, cow, horse, dog, cat mouse, or rat.

The condition to be treated can include any condition affecting a tooth or periodontium and is not limiting. Such conditions can include medical/dental diseases, ailments, structural conditions, and cosmetic/aesthetic problems. In some embodiments, the condition affecting the tooth or periodontium can include inflammation, pulpitis, infection, pain, sensitivity, caries (tooth decay), structural loss, gingivitis, periodontitis, periodontal disease, pericoronitis, and osteoradionecrosis, medication induced necrosis of the bone, degeneration, atrophy, abscess, and resorption.

In some embodiments, the condition to be treated is pain. In some embodiments, pain can be treated with a composition comprising biocompatible magnetic, magnetizable, or magnetically responsive agents and effective amounts of one or more of analgesic agents and/or anesthetic agents.

In some embodiments, the condition to be treated is caries (tooth decay). In some embodiments, caries can be treated with a composition comprising biocompatible magnetic, magnetizable, or magnetically responsive agents and effective amounts of one or more remineralizing agents. In some embodiments, the therapeutic agent includes one or more of fluoride, hydroxyapatite, therapeutic proteins such as amelogenin, and/or bioglass.

In some embodiments, the condition to be treated is inflammation. In some embodiments, inflammation can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is infection. In some embodiments, infection can be treated a composition comprising biocompatible magnetic, magnetizable, or magnetically responsive agents and effective amounts of one or more antibiotics.

In some embodiments, the condition to be treated is structural loss. In some embodiments, structural loss can be treated a composition comprising biocompatible magnetic, magnetizable, or magnetically responsive agents and effective amounts of one or more bonding agents/adhesives. In some embodiments, the structural loss is treated with effective amounts of BisGMA/Adhesive.

In some embodiments, the condition to be treated is gingivitis. In some embodiments, gingivitis can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is periodontitis. In some embodiments, periodontitis can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is periodontal disease. In some embodiments, periodontal disease can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is pericoronitis. In some embodiments, pericoronitis can be treated with a composition comprising biocompatible magnetic, magnetizable, or magnetically responsive agents and effective amounts of one or more antibiotics.

In some embodiments, the condition to be treated is osteoradionecrosis. In some embodiments, osteoradionecrosis can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is medication induced necrosis of the bone. In some embodiments, medication induced necrosis of the bone can be treated with a composition comprising biocompatible magnetic, magnetizable, or magnetically responsive agents and effective amounts of one or more anti-inflammatory agents, an immunosuppressant, an analgesic, an antibiotic, an antibacterial, and/or an anti-fungal agent.

In some embodiments, the condition to be treated is atrophy. In some embodiments, atrophy can be treated with a composition comprising biocompatible magnetic, magnetizable, or magnetically responsive agents and effective amounts of one or more therapeutic proteins, recombinant DNA, and/or recombinant RNA.

In some embodiments, the condition to be treated is resorption. In some embodiments, resorption can be treated with a composition comprising biocompatible magnetic, magnetizable, or magnetically responsive agents and effective amounts of one or more therapeutic proteins, recombinant DNA, and/or recombinant RNA. In some embodiments, the condition to be treated is dentinal hypersensitivity or sensitivity. Dentinal hypersensitivity and sensitivity are used interchangeably. Approximately 40-80% of the population suffers from tooth sensitivity. Dentinal tubules house nerve endings and thus, they are important in conduction of information regarding temperature changes and the presence of mechanical forces. Dentinal sensitivity occurs primarily due to exposed dentinal tubules and the presence of thin and porous enamel. The movement of fluid in dentinal tubules is thought to activate free nerve endings. This sensitivity can be characterized by momentary, sharp-shooting pain arising from exposed dentin in response to various stimuli, such as thermal, mechanical, osmotic or chemical elements. In the present invention, magnetic, magnetizable, or magnetically responsive agents can be used to occlude dentinal tubules. The magnetic, magnetizable, or magnetically responsive agents can be delivered into dentinal tubules to treat dentinal hypersensitivity using magnetic forces and can be used passively (without therapeutic agents) or can be used to deliver therapeutic agents, such as fluoride, hydroxyapatite, desensitizing agents and/or remineralizing agents to the dentinal tubules and areas of thin porous enamel. In some embodiments, the magnetic, magnetizable or magnetically-responsive agents have a size capable of occluding the dentinal tubules and treating the sensitivity. In some embodiments, the magnetic, magnetizable or magnetically-responsive agents reduce fluid movement in dentinal tubules and reduce nerve stimulation. In some embodiments, the magnetic, magnetizable or magnetically-responsive agents have a size ranging from about 20 nm to about 2000 nm. In some embodiments, the magnetic, magnetizable or magnetically-responsive agents have a size of at least about 300 nm. In some embodiments, the magnetic, magnetizable or magnetically-responsive agents have a size ranging from about 300 nm to about 2000 nm. In another embodiment, the size ranges from about 300 nm to about 1200 nm. In another embodiment, the size ranges from about 300 nm to about 1000 nm. Magnetic, magnetizable or magnetically-responsive agents in this application can be used without therapeutic agents attached but can also be attached to one or more therapeutic agents, such as fluoride, KCl, and apatites that also help mineralize the tooth structures. In some embodiments, one or more therapeutic agents are bound to the agents to treat hypersensitivity. In some embodiments, effective amounts of one or more desensitizing agents, one or more remineralizing agents and combinations thereof are added.

In some embodiments, the condition to be treated is periodontal disease. Periodontal disease is mainly the results of infections and inflammation of the gums and bone that surround and support the teeth. In some embodiments, magnetic, magnetizable or magnetically-responsive agents can be coated with one or more antibiotic agents, anti-inflammatory agents, anti-bacterial agents, antibodies against biological antigens, or a combination and can be applied in the periodontal pocket and steered into the pocket to the desired location, which can include hard to reach locations.

In some embodiments, the condition to be treated is an oral infection such as a refractory oral infection, for example, pericoronitis, or osteoradionecrosis, or medication-induced necrosis of the bone. They can be applied to the affected site and pulled into bone to dispense one or more antibiotic agents, anti-bacterial agents, or antibodies against biological antigens, anti-inflammatory agents or combinations thereof to treat the affected areas.

In some embodiments, the magnetic, magnetizable or magnetically-responsive agents are targeted to migrate to the pulp tissue. In some embodiments, the condition to be treated can include pulpitis, pain, infection and inflammation. In some embodiments, the magnetic, magnetizable or magnetically-responsive agent composition comprises one or more therapeutic agents selected from a remineralizing agent, a restorative/bonding material, an anti-inflammatory agent, an analgesic, an antibody, an antibiotic, an immunosuppressant, an antibacterial, an anti-fungal, a dental anesthetic, a desensitizing agent, recombinant RNA, recombinant DNA, lipopolysaccharides, a therapeutic protein, and combinations thereof. In some embodiments, the size of the magnetic, magnetizable or magnetically-responsive agents range from about 50 nm to about 1500 nm. In some embodiments, the treatment of the pulp reduces or eliminates the need for root canal treatment. In some embodiments, the pulp is treated before ischemic necrosis occurs. In some embodiments, the external magnetic field is applied from about 5 minutes to about 60 minutes to deliver the magnetic, magnetizable or magnetically-responsive agents to the pulp.

In some embodiments, the methods of the invention can be used to increase the bond strength of dental restorative materials and/or cements to tooth structures. Contemporary dental restorations and cements rely on micromechanical retention using dentinal tubules. In the present invention, in some embodiments, magnetic, magnetizable, or magnetically responsive agents can be delivered to dentinal tubules to improve the shear bond strength of composite resin (esthetic dental filling) to dentin. A lack of bond strength is a significant clinical problem in the field of restorative dentistry. In some embodiments, magnetic, magnetizable, or magnetically responsive nanoparticles can be mixed with composite bonding agents (available commercially) and one or more magnets can be used to pull the bonding agent into dentinal tubules for a period of time, e.g., from about 30 seconds to about 60 minutes, or from about 3-15 minutes. In some embodiments, the magnetic, magnetizable, or magnetically responsive nanoparticles have a size ranging from about 100 to about 1500 nm. In some embodiments, the magnetic, magnetizable, or magnetically responsive nanoparticles have a size ranging from about 300 to about 1500 nm. In some embodiments, the magnetic, magnetizable, or magnetically responsive nanoparticles have a size ranging from about 100 to about 1000 nm. In some embodiments, the magnetic, magnetizable, or magnetically responsive nanoparticles have a size of about 1000 nm. In some embodiments, the composite bonding agents include one or more agents shown in Table 1. In some embodiments, the bonding agent non-covalently couples with the magnetic, magnetizable or magnetically-responsive agents. In some embodiments, the amount of bonding agent to nanoparticle can range from 1:100 to 100:1 (weight to volume). In some embodiments, the amount of bonding agent to nanoparticle can range from 1:100 to 1:10 (weight to volume). In some embodiments, the magnetic, magnetizable or magnetically-responsive agents are mixed with the bonding agent in a ratio of about 1:10 (weight to volume). As shown below in Example 3, in some embodiments, this method can double the shear bond strength of composite compared to controls (unmodified bonding agent and no magnetic force) and in controls with modified bonding agent and no magnetic force. See FIG. 5.

The size of the magnetic, magnetizable, or magnetically responsive agents that are used to treat a condition affecting a tooth or periodontium, such as inflammation, pulpitis, infection, pain, sensitivity, caries (tooth decay), structural loss, gingivitis, periodontitis, periodontal disease, pericoronitis, and osteoradionecrosis, medication induced necrosis of the bone, degeneration, atrophy, abscess, and resorption is not limiting, provided that the agents have a size that is sufficient to migrate in response to an externally applied magnetic field to a desired location in the tooth or periodontium. In some embodiments, the magnetic, magnetizable, or magnetically responsive nanoparticles have a size ranging from about 1 nm to about 2000 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1500 nm. Average diameters will in some embodiments range from about 10 nm to about 1500 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, from about 800 nm to about 1000 nm, from about 1000 nm to about 1500 nm, or from about 1500 nm to about 2000 nm. The sizes of the agents listed above include the size of any magnetic, magnetizable, or magnetically responsive core and any coating thereon, if present.

In some embodiments of the method, the affected tooth can be isolated with a rubber dam prior to administering the composition comprising the composition.

In another embodiment, the present invention relates to a method for performing a restoration on a tooth with a cavity comprising applying an external magnetic field of about 0.1 to 3.0 Tesla to magnetic, magnetizable, or magnetically responsive agents in the size range of about 1 nm to 2000 nm coated with a dentin bonding agent which are loaded onto the tooth and wherein the agents (particles) are pulled down through the dentin tubules and into the pulp of the tooth by placing a magnetic system underneath the jaw to direct agents (particles) into the pulp of the lower teeth.

In another embodiment, the present invention relates to a method for treating dental sensitivity comprising pulling magnetic, magnetizable, or magnetically responsive particles, which are about 1 nm to 1 μm in size, into the dentin tubules of a tooth with an external magnetic field of about 0.1 to 3.0 Tesla which is applied for about 1 to 60 minutes and wherein the nanoparticles can be formulated to include a medication, fluoride, hydroxyapatite, a desensitizing agent or a remineralizing agent.

In another embodiment, the present invention relates to a method for treating a dental infection comprising pulling magnetic, magnetizable, or magnetically responsive particles into the dentin tubules of a tooth with an external magnetic field of about 0.1 to 3.0 Tesla which is applied for about 1 to 60 minutes and wherein the nanoparticles are formulated with an antimicrobial agent which can eradicate a bacterial infection at the site of infection. In some embodiments, the antimicrobial agent is selected from the group comprising penicillin, ampicillin, amoxicillin, azithromycin, metronidazole, clindamycin, tetracycline, cephalosporin, erythromycin, ofloxacin and other quinolones and vancomycin.

In another embodiment, the present invention relates to a method for treating inflammation including pulpitis comprising pulling magnetic, magnetizable, or magnetically responsive particles into the dentin tubules of a tooth with an external magnetic field of about 0.1 to 3.0 Tesla which is applied for about 1 to 60 minutes and wherein the nanoparticles with a diameter size of about 1 to 2000 nm are formulated with an agent, such as an anti-inflammatory agent and/or an antibiotic which can eradicate pulpitis at the site of infection.

In another embodiment the present invention relates to a method for improving a dental restoration of a tooth comprising formulating a composite material used in the restoration with magnetic, magnetizable, or magnetically responsive particles and pulling the composite material into the dentin tubules with an external magnetic system thereby preventing shrinkage of the composite material away from the tooth structure and wherein the magnetic field strength is about 0.1 to 3 Tesla.

In another embodiment, the present invention relates to a method for improving a dental restoration of a tooth comprising i) formulating a composite material or resin used in the restoration with magnetic, magnetizable or magnetically responsive particles about 25 nm to 2000 nm in size and ii) pulling the composite material into the dentin tubules with an external magnet or magnetic system and wherein the magnetic field strength is about 0.1 to 3 Tesla or in a more preferred magnetic field strength of about 0.5 to 1.5 Tesla.

In another embodiment, the present invention relates to a method for treating dental infections, inflammation, sensitivity and performing dental restorations comprising isolating the affected tooth with a rubber dam and applying the particles onto the surface of the affected tooth or area which can be in a gel, paste or an aqueous film or surfactant and positioning the magnetic system to apply a vertical pulling force that is parallel to the direction of the dentinal tubules of the affected tooth and wherein the magnetic, magnetizable or magnetically responsive agents/particles are in a solution of 10 to about 500 microliters are applied to the affected tooth surface using a syringe and spread using a brush or by another means such as by hand or a device. In some embodiments, the magnetic system will be left in place for about 1 to 60 minutes and the agents will be periodically added to the affected area using a syringe and brush as needed. At the end of the procedure, the affected tooth is washed and excess material is removed using dental suction.

In some embodiments, the invention provides a dental delivery system for delivering one or more therapeutically effective agents to a desired location in a subject's tooth or periodontium comprising i) one or more magnets capable of applying an external magnetic field; and
ii) a composition comprising biocompatible magnetic, magnetizable, or magnetically responsive agents; wherein the magnetic, magnetizable, or magnetically responsive agents migrate to a desired location in response to the externally applied magnetic field.

In another embodiment, the present invention relates to a dental delivery system for treating pulpitis comprising magnetic, magnetizable, or magnetically responsive agents with a size of about 1 nm to 1 mm, from about 1 nm to about 1500 nm, or from about 10 nm to about 1000 nm, coated with a polymer or polysaccharide matrix, such examples might include chitosan or starch and a therapeutic agent such as an antibiotic, an anti-inflammatory agent or a drug eluting agent and an external magnetic field strength of about 0.1 to 3.0 Tesla.

In some embodiments, the composition comprising the magnetic, magnetizable, or magnetically responsive agents is applied to a tooth cavity. In some embodiments, the composition is applied to a surface of dentin in cases where the condition affecting the tooth includes inflammation, infection, pain, sensitivity, caries (tooth decay), or structural loss. In some embodiments, a cavity is prepared in the tooth to expose dentin and the composition is applied to the dentin. In some embodiments, the depth of the cavity is at least about 0.5 mm. In some embodiments, the depth of the cavity is at least about 1 mm. In some embodiments, the depth of the cavity is at least about 1.5 mm. In some embodiments, the depth of the cavity is at least about 2 mm.

In some embodiments, the composition is applied to a periodontal pocket in cases where the condition is gingivitis, periodontitis, periodontal disease, pericoronitis, osteoradionecrosis, medication induced necrosis of the bone, degeneration, atrophy, abscess, and resorption.

The composition can be applied to the tooth or periodontium using any suitable means. In some embodiments, the composition is applied using a brush, syringe, dropper, pipette, or other appropriate dispenser. In another embodiment, for example, when applying to the upper teeth or upper periodontium, the composition is applied using a mouthpiece comprising the agents.

In another embodiment the invention relates to a method for producing magnetic, magnetizable or magnetically responsive particles/agents for use in dentistry comprising:

i) obtaining the magnetic, magnetizable, or magnetically responsive agents in the size range of about 1 to 2000 nm in diameter,
ii) coating the agents with a polymer, negatively or positively charged, which may include polysaccharides (starch, chitosan, polyethylene glycol) that render these particles biocompatible, and either acts as a weak cation exchanger or allows covalent coupling of therapeutic agents of interest, silane-coupling agent, hydroxyapatite or fluoride, and
iii) bonding another agent or material of interest such as an antibiotic, anti-inflammatory agent, tooth desensitizing agent for use in treating dental infections, inflammation, sensitivity, and for use in dental restorations.

II. Compositions Comprising Magnetic, Magnetizable, or Magnetically Responsive Agents Each and every one of the compositions described herein can be used in each and every one of the methods and systems of the invention.

In some embodiments, the invention provides a composition for treating a condition affecting a tooth or periodontium in a subject comprising biocompatible magnetic, magnetizable, or magnetically responsive agents. In some embodiments, the composition comprises an effective amount of a therapeutic agent. In some embodiments, the therapeutic agent is selected from the group consisting of a remineralizing agent, a restorative/bonding material, an anti-inflammatory agent, an immunosuppressant, an analgesic, an antibody, an antibiotic, an antibacterial, an anti-fungal, a dental anesthetic, a desensitizing agent, recombinant RNA, recombinant DNA, lipopolysaccharides, a therapeutic protein, and combinations thereof.

In another embodiment the present invention relates to a composition comprising a magnetic, magnetizable, or magnetically responsive particle coated with an antimicrobial agent, colorant, restoration scaffold, stem cells, steroids, or a contrast material.

In some embodiments, the invention relates to a composition comprising magnetic, magnetizable or magnetically-responsive agents coated with eluting or otherwise including a dentin bonding material or agent or a therapeutic agent, and a magnetic system for directing those particles into or through the tooth to at least one desired location.

The magnetic, magnetizable, or magnetically responsive agents are not limiting. The agents can be particles, fluid, rods, cubes, liposomes or agents of other shape that are magnetic or are associated with magnetizable or magnetically responsive materials (e.g., paramagnetic, ferromagnetic, ferrimagnetic or superparamagnetic materials). They can be simple aggregations of molecules or they can be structured into two or more layers of different substances. For example, simple nanoparticles consisting of magnetite or maghemite are suitable for use. See, e.g., *Scientific and Clinical Applications of Magnetic Microspheres*, U. Hafeli, W. Schutt, J. Teller, and M. Zborowski (eds.) Plenum Press, New York, 1997; and Tiefenauer et al., *Bioconjugate Chem.* 4:347, 1993. More complex agents can consist of a core made of one substance and one or more shells made of another substance(s). In some embodiments, the agents comprise a magnetic, magnetizable, or magnetically responsive core.

Exemplary core materials that are suitable for inclusion in a magnetic, magnetizable, or magnetically responsive agent include ferrites of general composition $MeO_xFe_2O_3$ where Me is a bivalent metal such as Co, Mn or Fe. Other suitable materials are nickel ferrite, $NiFe_2O¬_4$, $\gamma Fe_2O_3$, $Fe_3O_4$ (also known as magnetite), the pure metals Co, Fe, Ni, and metal compounds such as carbides and nitrides. The core material is generally an MRI contrast agent. In some embodiments, the magnetic, magnetizable, or magnetically-responsive component of the particles can be made of iron, iron oxide, nickel, cobalt, and their combination and can be modified with carbon, gold, silver, gadolinium, and other elements. In some embodiments, the core comprises one or more of iron, cobalt and nickel.

Many different type of small particles (nanoparticles or micron-sized particles) are commercially available from several different manufacturers including: Chemicell (Berlin, Germany), OZ Biosciences (San Diego, CA), Biopal (Worcester, MA), GeccoDots (Lund, Sweden), BioLite, OceanNanoTeach (San Diego, CA), Bangs Laboratories (Fishers, Ind.), Promega (Madison, Wis.), Dynal Inc. (Lake Success, N.Y.), Advanced Magnetics Inc. (Surrey, U.K.), CPG Inc. (Lincoln Park, N.J.), Cortex Biochem (San Leandro, Calif.), European Institute of Science (Lund, Sweden), Ferrofluidics Corp. (Nashua, N.H.), FeRx Inc.; (San Diego, Calif.), Immunicon Corp.; (Huntingdon Valley, Pa.), Magnetically Delivered Therapeutics Inc. (San Diego, Calif.), Miltenyi Biotec GmbH (USA), Microcaps GmbH (Rostock, Germany), PolyMicrospheres Inc. (Indianapolis, Ind.), Scigen Ltd. (Kent, U.K.), Seradyn Inc. (Indianapolis, Ind.), and Spherotech Inc. (Libertyville, Ill.). Such particles can be made using conventional techniques, such as grinding and milling, emulsion polymerization, block copolymerization, and microemulsion.

The size of the magnetic, magnetizable, or magnetically responsive agents is not limiting provided that they are able to migrate to a desired location in the tooth or periodontium using an externally applied magnetic field. In some embodiments, the magnetic, magnetizable or magnetically-responsive agent can vary from 1 nm to 2000 nm diameter in size. Larger agents can contain more magnetically responsive material, e.g., more iron and thus would exhibit greater magnetic transport forces. Smaller agents can experience smaller tissue resistance forces when moving through tooth material or when moving through gaps or dentin tubules in the tooth. One of skill in the art would recognize that there can be a best choice for agent size so that the ratio of applied magnetic force versus tooth resistance forces is maximized. In one embodiment, a 1 nm to a 500 nm diameter size of iron-core particles is effective to allow a magnetic system to transport particles through teeth to the underlying pulp. In some embodiments, the size of the magnetic, magnetizable, or magnetically responsive agents are large enough to experience significant magnetic forces under an applied magnetic field, but small enough to be able to transport through the dentinal tubules of the tooth or through the periodontium. In some embodiments, the agents have a size of from about 50 nm to about 1500 nm. The agents for use in a subject method generally have a mean size in a range of from about 1 nm to about 2000 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1500 nm. Average diameters will in some embodiments range from about 10 nm to about 1500 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, from about 800 nm to about 1000 nm, from about 1000 nm to about 1500 nm, or from about 1500 nm to about 2000 nm. The sizes of the agents listed above include the size of any magnetic, magnetizable, or magnetically responsive core and any coating thereon, if present.

In some embodiments, the magnetic core particle can have a diameter of from about 1 nm to about 1000 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, or from about 800 nm to about 1000 nm. In some embodiments, the magnetic domains for iron cores are at most 40 nm.

In some embodiments, the magnetic, magnetizable, or magnetically responsive agents or core are enclosed within a liposome.

In some embodiments, the magnetic, magnetizable, or magnetically responsive agents are nanoparticles and comprise an iron core. In some embodiments, the nanoparticles are superparamagnetic iron oxide nanoparticles (SPION). In some embodiments, the magnetic, magnetizable, or magnetically responsive agent is a single-core nanoparticle having a 20-40 nm iron oxide bead inside as the core.

In some embodiments, the compositions comprising biocompatible magnetic, magnetizable, or magnetically responsive agents comprise effective amounts of one or more therapeutic agents. The therapeutic agents described herein encompass active agents and pharmaceutically acceptable salts, solvates, hydrates, prodrugs, and metabolites thereof. In some embodiments, the therapeutic agent is selected from the group consisting of a remineralizing agent, a restorative/bonding material, an anti-inflammatory agent, an analgesic, an antibody, an antibiotic, an immunosuppressant, an antibacterial, an anti-fungal, a dental anesthetic, a desensitizing agent, recombinant RNA, recombinant DNA, lipopolysaccharides, a therapeutic protein, and combinations thereof.

In some embodiments, the composition comprises an effective amount of a desensitizing agent selected from the group consisting of glutaraldehyde, silver nitrate, zinc chloride, strontium chloride hexahydrate, sodium fluoride, stannous fluoride, strontium chloride, potassium oxalate, calcium phosphate, calcium carbonate, bio active glasses (e.g., SiO2-P2O5-CaO—Na2O), fluoride varnishes, oxalic acid and resin, glass ionomer cements, composites, dentin bonding agents, propolis and combinations thereof.

In some embodiments, the composition comprises an effective amount of an antibiotic selected from the group consisting of tetracycline, demeclocycline, doxycycline, minocycline, lymecycline, oxytetracycline, triclosan, penicillin, penicilline V, phenoxymethylpenicillin, flucloxacillin, amoxicillin, cephalosporins, cefaclor, cefadroxil, cephalexin, aminoglycoside, gentamicin, tobramycin, macrolide, erythromycin, azithromycin, clarithromycin, clindamycin, vancomycin, sulfonamide, trimethoprim, co-trimoxazole, metronidazole, tinidazole, quinolone, ciprofloxacin, levofloxacin, norfloxacin, ofloxacine and combinations thereof.

In some embodiments, the composition comprises an effective amount of an anti-inflammatory agent selected from the group consisting of a non-steroidal anti-inflammatory agent, a corticosteroid, aspirin, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, hydrocortisone, cortisone, ethamethasoneb, prednisone, prednisolone, triamcinolone, methylprednisolone, aldosterone, betamethasone, dexamethasone, mineralocorticoid, fludrocortisone and combinations thereof.

In some embodiments, the composition comprises an effective amount of an immunosuppressant. An immunosuppressant can be useful in treating chronic pulpal inflammation. In some embodiment, the immunosuppressant is selected from the group consisting of cyclosporine, FK506 and combinations thereof.

In some embodiments, the composition comprises an effective amount of an analgesic agent selected from the group consisting of opioids, codeine, fentanyl, hydrocodone, hydromorphone, propofol, meperidine, methadone, morphine, oxycodone, non-opioids, tramadol and combinations thereof.

In some embodiments, the composition comprises an effective amount of an anesthetic selected from the group consisting of benzocaine, chloroprocaine, cocaine, cyclomethycaine, dimethocaine/larocaine, piperocaine, propoxycaine, procaine/novocaine, proparacaine, tetracaine/amethocaine, articaine, bupivacaine, cinchocaine/dibucaine, etidocaine, levobupivacaine, lidocaine/lignocaine, mepivacaine, prilocaine, ropivacaine, trimecaine, saxitoxin, neosaxitoxin, tetrodotoxin, menthol, eugenol and combinations thereof.

In some embodiments, the composition comprises an effective amount of an anti-fungal agent selected from the group consisting of nystatin, amphotericin B, ketoconazole, miconazole and combinations thereof.

In some embodiments, the composition comprises an effective amount of chlorhexidine as an antibacterial agent.

In some embodiments, the composition comprises an effective amount of a bonding/restorative agent. The bonding agent is not limiting and can include those commercially available bonding agents to bond tooth filling materials to tooth structure. In some embodiments, the bonding agents can include any of the agents shown in the table below.

TABLE 1

| Classification | Material | Company |
|---|---|---|
| Etch and Rinse | Admira Bond | VOCO, Germany |
| | Scotchbond Multi-Purpose | 3M ESPE, USA |
| | Adper Single Bond | 3M ESPE, USA |
| | Clearfil LB | Kurary, Japan |
| | All Bond 2 | Bisco, USA |
| | Gluma 2000 | |
| | One Step | Bisco, USA |
| | One Step Plus | Bisco, USA |
| | Optibond Dual Cure | Kerr USA |
| | Optibond Solo | Kerr, USA |
| | Optibond FL | Kerr, USA |
| | Permagen | Ultradent, USA |
| | Syntac Classic | lvoclar-Vivadent, Liechtenstein |
| | Sinale Bond | 3M ESPE, USA |
| | Denthesive | Heraeus Kulzer, Germany |
| | Gluma Solid Bond | Heraeus Kulzer, Germany |
| | Bond-1 SF | Pentron |
| | Bond-1 C&B | Pentron |
| | Amalgambond Plus | Parkell |
| | TotalBond | Parkell |
| | Prime & Bond | Dentsply, USA |
| | IntegraBond | Premier, USA |
| | Esteem | Bosworth, USA |
| | Cararesin Bond | Shofu, USA |
| | DenTASTIC | PULPDENT |
| Self-Etch Primer | ART Bond | Coltene, Switzerland |
| | PUB 3 | Dentsply, USA |
| | Clearfil SE | Kurary, Japan |
| | Clearfil Protect Bond | Kurary, Japan |
| | Denthesive 2 | Heraeus Kulzer, Germany |
| | Tvrian SPE | Bisco |
| Self-Etch Adhesive | Clearfil S3 Bond | Kurary, Japan |
| | G Bond | GC Corp, Japan |
| | AQ Bond Plus | Sun Medicals |
| | Hybrid Bond | lvoclar-Vivadent, Liechtenstein |
| | All Bond SE | Bisco, USA |
| | iBond Gluma inside | Heraeus Kulzer, Germany |
| | Fluorobond Shake One | Tokuyama Coro, Japan |
| | PSA Dyract | Dentsply, USA |
| | Adper Prompt L-Pop | 3M ESPE, USA |
| | Prompt L-Pop | 3M ESPE, USA |
| | ADD & BOND | Parkell |

TABLE 1-continued

| Classification | Material | Company |
|---|---|---|
| | Brush&BOND | Parkell |
| | MetaSeal | ParkeII |
| | DuraFinish & DuraFinish ALL-CURE | Parkell |
| | aladdin Total Etch | Sultan HealthCare |
| | PermaCem | DMG America, USA |
| | BeautyBond | Shofu, USA |
| | FL-Bond II | Shofu, USA |
| | Prelude | Danville Engineering Inc. |

In some embodiments, the composition comprises effective amounts of one or more of the following: hydroxyapatite, calcium titanate, potassium chloride, ceramics, Bis-GMA/dental adhesives, zinc, silver, gold, capsaicin, amelogenin or silane.

In some embodiments, salts of the active agents such as acetate or phosphate salts are used to bind the active agents to the magnetic, magnetizable or magnetically-responsive agents. In some embodiments, the therapeutic agent comprises prednisolone phosphate, sulfacetamide sodium, prednisolone acetate, triamcinolone acetonide, dexamethasone phosphate or dexamethasone acetate. In some embodiments, the salt is converted to the active agent before binding, e.g., to a cell receptor.

Effective amounts of the therapeutically active agents to be administered in the compositions can be determined without undue experimentation using existing knowledge and skill in the art about the therapeutic agents and standard dose-response protocols. In one embodiment, the amount of the therapeutically active agent can vary from about 0.00001 μg/kg body weight to about 100 mg/kg body weight. This includes all values and subranges therebetween, including 0.00001, 0.00002, 0.00003, 0.00004, 0.00005, 0.00006, 0.00007, 0.00008, 0.00009, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, and 0.01 μg/kg, 0.02, 0.03, 0.04, 0.05, 0.06, 0.07, 0.08, 0.09, and 0.1 μg/kg, 0.2, 0.3, 0.4, 0.5, 0.6, 0.7, 0.8, 0.9, and 1.0 μg/kg, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1 2, 3, 4, 5, 6, 7, 8, 9, 1.0. 1.5 2.0, 2.5, 5.0, 7.5, 10, 20, 30, 40, 50, 60, 70, 80, 90, and 100 mg/kg, and any combination thereof.

The frequency of administration of the compositions can be determined without undue experimentation using standard dose-response protocols. In one embodiment, the composition is administered in a single administration over a timecourse of about 30 seconds to 3 hrs. In some embodiments, the composition is administered more than one time, for example, on 2, 3, 4, 5, 6, 7, 8, 9, 10 or more occasions, and the interval between each administration can be about 1 minute, about 5 minutes, about 10 minutes, about 20 minutes, about 30 minutes, about 60 minutes, about 2 hours, about 4 hours, about 8 hours, about 24 hours, about 2 days, about 3 days, about 4 days, about 5 days, about 6 days, about 1 week, about 2 weeks, about 3 weeks, about 4 weeks, or longer. The administration can be suitably adjusted in the case a controlled or sustained release formulation is used. The compositions for administration can be made without undue experimentation by means well known in the art, for example with pharmaceutically acceptable carrier or excipient for example, an inert diluent, solvent, suspending agent or the like.

In some embodiments, the one or more therapeutic agents are bound to the magnetic, magnetizable, or magnetically responsive agents. In some embodiments, the therapeutic agent is bound to the magnetic, magnetizable, or magnetically responsive agents chemically, ionically, covalently, non-covalently, using a thin film rehydration method, by dialysis, by mechanical absorption polymerization or a combination thereof. In some embodiments, the therapeutic agent can be chemically attached directly or indirectly (using a linker) to the magnetic, magnetizable, or magnetically responsive agents. In some embodiments, binding of the therapeutic agent encompasses being absorbed or impregnated within a coating, such as a matrix or polymer of the magnetic, magnetizable, or magnetically responsive agents. The magnetic, magnetizable, or magnetically responsive agents can be bound to the therapeutic agents using known techniques and methods.

In another embodiment, the present invention relates to a composition comprising a magnetic, magnetizable or magnetically responsive agent coated with a polymer or polysaccharide, e.g., chitosan, starch and/or a silane-coupling agent that can be used to couple the therapeutic agent, such as a bonding agent, drug, steroid, an anti-inflammatory agent, tooth desensitizing agent or other therapeutic agents to the magnetic, magnetizable or magnetically responsive agent.

In some embodiments a thin-film rehydration method is used for binding the therapeutic agent. In some embodiments lipids, therapeutic agents and the magnetic, magnetizable, or magnetically responsive agents are first mixed in an organic solvent to assure a clear and homogeneous mixture of lipids. Once the lipids are thoroughly mixed in the organic solvent, the solvent is removed to yield a lipid film. The lipid film is thoroughly dried to remove residual organic solvent by placing the solution in a vacuum desiccator for 1 hour to 24 hours. An aqueous medium is added to the container of dry lipid and agitated. The temperature of the hydrating medium should be above the gel-liquid crystal transition temperature (Tc or Tm) of the lipid with the highest Tc before adding to the dry lipid. The hydrated lipid suspension is then downsized by a variety of techniques, including sonication or extrusion.

In some embodiments, a mechanical absorption polymerization method is used for binding. In this embodiment, the therapeutic agent and the magnetic, magnetizable, or magnetically responsive agents are placed together in solution, and incubated for a period of time, preferably at low temperature such as 4° C., resulting in adhesion of the therapeutic molecule to the magnetic, magnetizable, or magnetically responsive agents. See, e.g., Jiang et al., *Int J Nanomedicine.* 2009; 4: 107-114; Cheng et al., *Int J Nanomedicine.* 2011; 6: 2183-2189. In some embodiments, the therapeutic agent bound by this method is a lipophilic compound.

In some embodiments, the magnetic, magnetizable, or magnetically responsive agents have a coating, e.g., a biocompatible substance. In some embodiments, the coating can have a thickness (e.g., the average distance from the outside surface of the core magnetic particle to the outside surface of the coating) of from about 1 nm to about 2000 nm. In some embodiments the coating is about 1 nm to about 1500 nm, e.g., from about 1 nm to about 50 nm, from about 50 nm to about 100 nm, from about 100 nm to about 150 nm, from about 150 nm to about 200 nm, from about 200 nm to about 250 nm, from about 250 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, from about 900 nm to about 1000 nm, from about 1000 nm to about 1250 nm, from about 1250 nm to about 1500.

In some embodiments, the ratio of the thickness of the diameter of the magnetic core particle to the thickness of the coating is from about 1:0.1 to about 1:100, e.g., from about 1:0.1 to about 1:1, from about 1:1 to about 1:5, from about 1:5 to about 1:10, from about 1:10 to about 1:25, from about 1:25 to about 1:50, from about 1:50 to about 1:100.

The coating is not limiting, provided it is biocompatible. In some embodiments, the coating is a biocompatible substance such as a lipid, charged lipid, biocompatible polymer or polysaccharide matrix. In some embodiments, the biocompatible substance forms a shell around a magnetic, magnetizable, or magnetically responsive core. In some embodiments, the biocompatible substance is selected from chitosan, silane, amine silane, glucuronic acid, citric acid, starch, DAEA, dextran, dextran-sulfate, polyaspartic acid, polyacrylamide, polyacrylic acid, polydimethylamine, polyethylene glycol, poly(lactic-co-glycolic acid), hyaluronan, hyaluronic acid, polydopamine carboxymethyldextran, dialdehyde starch, chitin, alginate, cellulose, carboxymethylcellulose; proteins or derivatives thereof, such as albumins, peptides, synthetic polypeptides, and polypeptides modified with a non-amino acid group such as a sugar, a lipid, a polysaccharide, a phosphate group, etc.; synthetic polymers, polyvinylpyrrolidone, polyethyleneimine, polymethacrylates, bifunctional carboxylic acids and derivatives thereof, such as mercaptosuccinic acid or hydroxycarboxylic acids, and combinations thereof and radioactive or fluorescently labeled versions of any of the foregoing.

In some embodiments, the therapeutic agent can be linked with the core and/or biocompatible substance either directly or indirectly, or absorbed or impregnated on the surface and/or within the shell of the biocompatible substance. In some embodiments, the therapeutic agent exhibits, delayed, controlled or sustained release over a period of time.

A typical process for adding therapeutic agents to coated magnetizable, or magnetically responsive agents, such as nanoparticles involves treating the agents with a silanizing agent that reacts with and couples a chemical group to the surface of the magnetic, magnetizable, or magnetically responsive agents. The chemical group can serve as a substrate to which therapeutic agents can be coupled. For example, in an exemplary method, silica-coated nanoparticles are prepared and the particle surfaces are silanized using trimethylsilylpropyl-diethylenetriamine (DETA), a silanization agent that attaches primary amine groups to silica surfaces. Antibodies, proteins or other active agents can then be covalently coupled to the silanized surface using the cyanogen bromide (CNBr) method. As one example, CNBr-mediated coupling can be achieved by suspending silica-coated nanoparticles previously silanized with DETA in a 2 M sodium carbonate buffer and ultrasonicating the mixture to create a particle suspension. A solution of CNBr (e.g., 2 g CNBr/l ml acetonitirile) is then added to the particle suspension to activate the nano particles. After washing the nanoparticles with a neutral buffer (e.g., phosphate buffered saline, pH 8), an antibody solution is added to the activated nanoparticle suspension causing the antibodies to become bound to the nanoparticles. A glycine solution can also be added to the antibody-coated nanoparticles to block any remaining unreacted sites.

In some embodiments, the magnetic, magnetizable, or magnetically responsive agents are dextran coated. Magnetic nanoparticles can be made using any known process.

For example, magnetic iron-dextran particles can be prepared by mixing 10 ml of 50% (w/w) aqueous Dextran T-40 (Pharmacia) with an equal volume of an aqueous solution containing 1.51 g $FeCl_3$-6H2O and 0.64 g $FeCl_2$-$4H_2O$. While stirring, the mixture is titrated to pH 10-11 by the drop-wise addition of 7.5% (v/v) $NH_4OH$ heated to 60-65° C. in a water bath for 15 minutes. Aggregates are then removed by 3 cycles of centrifugation in a low-speed clinical centrifuge at 600·times·g for 5 minutes. The ferromagnetic iron-dextran particles are separated from unbound dextran by gel filtration chromatography on Sephacryl-300. Five ml of the reaction mixture is then applied to a 2.5·times·33 cm column and eluted with 0.1 M sodium acetate and 0.15 M NaCl at pH 6.5. The purified ferromagnetic iron-dextran particles collected in the void volume will have a concentration of 7-10 mg/ml as determined by dry weight analysis. Molday and Mackenzie (1982) Journal of Immunological Methods 52:353-367. Also see (Xianqiao (2003) China Particuology Vol. 1, No. 2, 76-79).

In some embodiments, suitable magnetic, magnetizable, or magnetically responsive agents have the formula: M-(L)-Z, the linkage sites between L and Z having covalently bound functional groups, wherein M represents the magnetic core particle, L represents an optional linker group, and Z represents a therapeutic agent. In other embodiments, a suitable magnetic nanoparticle is of the formula: M-S-(L)-Z, the linkage sites between S and L and L and Z having covalently bound functional groups, wherein M represents the magnetic core particle, wherein S represents a biocompatible substance fixed to M, wherein M represents the magnetic core particle, L represents an optional linker group, and Z represents a therapeutic agent. In some embodiments, a suitable magnetic nanoparticle is of the formula: M-(L)-Z, where M represents the magnetic core particle, where L represents an optional linker group, and where Z represents a therapeutic agent. In other embodiments, a suitable magnetic nanoparticle is of the formula: M-S-(L)-Z, where M represents the magnetic core particle, where S represents a biocompatible substance surrounding M or attached to M, where L represents an optional linker group, and where Z represents a therapeutic agent.

In some embodiments, a suitable magnetic nanoparticle comprises two or more different therapeutic agents attached to the same core particle or to the same biocompatible substance surrounding or attached to the core particle. For example, in some embodiments, a suitable magnetic nanoparticle is of the formula M-(L)-$Z_1Z_2$, or M-S-(L)-$Z_1Z_2$, where $Z_1$ and $Z_2$ are different therapeutic agents, where M is a magnetic core particle, and where L, if present, is a linker. In some embodiments, a suitable functionalized magnetic nanoparticle is of the formula M-S-(L)-$Z_1Z_2$, where M is a magnetic core particle, where the moieties $Z_1$ and $Z_2$ are each linked to the substrate(S), either directly or via a linker (L) (e.g., L, if present, is a linker). In some embodiments, a suitable magnetic nanoparticle comprises at least a third moiety $Z_3$. Thus, e.g., in some embodiments, a suitable magnetic nanoparticle is of the formula M-S-(L)-$Z_1Z_2Z_3$, where the moieties $Z_1$, $Z_2$, and $Z_3$ are each bound to the biocompatible substance, either directly or via a linker.

In some embodiments, the linker group L, if present, can be formed by reaction of a compound such as poly- and dicarboxylic acids, polyhydroxycarboxylic acids, a silanization agent, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

In some embodiments, the magnetic, magnetizable, or magnetically-responsive agents are formulated as pharmaceutical compositions. The compositions can comprise the magnetic, magnetizable, or magnetically-responsive agents described herein and can include one or more of the following: a salt; a buffer; a pH adjusting agent; a non-ionic detergent; a protease inhibitor; a nuclease inhibitor; and the like.

A pharmaceutical composition comprising magnetic, magnetizable, or magnetically-responsive agents will comprise one or more pharmaceutically acceptable carriers. As used herein, "pharmaceutically acceptable carrier" includes any material which, when combined with an active ingredient of a composition, allows the ingredient to retain biological activity and without causing disruptive reactions with the subject's immune system or other physiological function. Examples include, but are not limited to, any of the standard pharmaceutical carriers such as a phosphate buffered saline solution, water, emulsions such as oil/water emulsion, and various types of wetting agents. Exemplary carriers are phosphate buffered saline or normal (0.9%) saline. Compositions comprising such carriers are formulated by well-known conventional methods (see, for example, *Remington's Pharmaceutical Sciences*, Chapter 43, 14th Ed., Mack Publishing Col, Easton Pa. 18042, USA). Pharmaceutically acceptable excipients have been amply described in a variety of publications, including, for example, A. Gennaro (2000) "*Remington: The Science and Practice of Pharmacy,*" 20th edition, Lippincott, Williams, & Wilkins; *Remington's Pharmaceutical Sciences,* 14th Ed. or latest edition, Mack Publishing Col, Easton Pa. 18042, USA; *Pharmaceutical Dosage Forms and Drug Delivery Systems* (1999) H. C. Ansel et al., eds., 7.sup.th ed., Lippincott, Williams, & Wilkins; and *Handbook of Pharmaceutical Excipients* (2000) A. H. Kibbe et al., eds., 3.sup.rd ed. Amer. Pharmaceutical Assoc.

In some embodiments, the magnetic, magnetizable, or magnetically-responsive agents are present in a liquid composition at a concentration of from about 1 mg particle weight per ml to about 1 g particle weight per ml, e.g., from about 1 mg particle weight per ml to about 500 mg particle weight per ml, from about 2 mg particle weight per ml to about 250 mg particle weight per ml, from about 5 mg particle weight per ml to about 100 mg particle weight per ml, from about 7 mg particle weight per ml to about 50 mg particle weight per ml, from about 10 mg particle weight per ml to about 30 mg particle weight per ml, from about 12 mg particle weight per ml to about 25 mg particle weight per ml.

In some embodiments, the particles density by weight of iron (or other core material) per mL of water can range from about 2 mg (iron or other core material)/ml to about 100 mg (iron or other core material)/ml. In some embodiments, the particles density by weight of iron (or other core material) per mL of water can range from about 6 mg (iron or other core material)/ml to about 25 (iron or other core material) mg/ml. In some embodiments, the fill fraction of iron (or other core material) is around 20-30% by wt. In some embodiments, the ratio of iron (or other core material) mass to particle mass is about 2:5.

In some embodiments, the magnetic, magnetizable, or magnetically responsive agents can be mixed in with a gel or gel-like substance. In some embodiments, the gel is a poloxamer gel, for instance, which is liquid at room temperature and turns solid at body temperature, so that it would stay in the upper teeth once placed there.

In some embodiments, magnetic, magnetizable, or magnetically responsive agents are suspended in normal saline. In some embodiments, magnetic, magnetizable, or magnetically responsive agents are suspended in deionized water.

III. Magnets and Magnetic Configurations

The magnetic, magnetizable, or magnetically responsive agents are subjected to an applied external magnetic field in the methods and systems of the invention. The external magnetic field has a strength that is sufficient to induce the migration of the agents to a desired location in the tooth or periodontium.

The external magnetic field is achieved by one or more magnets that are positioned in a way that applies a force on the magnetic, magnetizable, or magnetically responsive agents. The magnetic system can be composed of permanent magnets, electromagnets, or a combination of both and can be designed and shaped to apply magnetic forces on the agents to deliver them into or through the teeth or periodontium to at least one desired location.

In one embodiment, the external magnetic field will pull magnetic, magnetizable, or magnetically-responsive agents into or through teeth to at least one desired target (e.g. the pulp). In order to generate the most effective magnetic forces on the agents, it is desirable to have the magnetic system be composed of strong magnets. For example, the system could contain permanent magnets of strength of about 0.1 to 3.0 Tesla. Such permanent magnets are commercially available. The system could also contain electromagnets, of similar strength. More generally, one skilled in the art would recognize that an effective system could contain magnets of strength between about 0.01 and 3.0 Tesla. In some embodiments, the external magnetic field has a strength of about 0.1 to about 3.0 Tesla. In some embodiments, the external magnetic field has a strength of about 1.2 Tesla. In some embodiments, the external magnetic field has a strength of about 0.1 to about 0.3 Tesla, about 0.3 to about 0.5 Tesla, about 0.5 to about 0.7 Tesla, about 0.7 to about 0.9 Tesla, about 0.9 to about 1.1 Tesla, about 1.1 to about 1.3 Tesla, about 1.3 to about 1.5 Tesla, about 1.5 to about 1.7 Tesla, about 1.7 to about 1.9 Tesla, about 1.9 to about 2.1 Tesla, about 2.1 to about 2.3 Tesla, about 2.3 to about 2.5 Tesla, about 2.5 to about 2.7 Tesla, or about 2.7 to about 3.0 Tesla.

Magnetic gradients (the rate of change of the magnetic field in space) create magnetic forces on magnetic, magnetizable, or magnetically-responsive agents, such as iron-core nanoparticles. A spatially-uniform magnetic field does not create appreciable forces on magnetic, magnetizable, or magnetically-responsive agents. Hence it is advantageous to have a magnetic field that both extends from the magnetic system to the agents but that also provides a strong magnetic gradient (that has a strong spatial variation). To achieve such a magnetic field, it is advantageous to choose the size of magnets or magnetic elements within the system to be of a similar size as the distance from the magnetic system to the agents. Since in dentistry applications, the magnetic system could be placed within a few centimeters (e.g. 0.5 to 10 cm) from the agents that will be used in the teeth of patients, the magnetic system should have magnets or magnetic elements that are approximately of this size (0.5 to 10 cm) to create strong magnetic fields that will both reach the agents and create high magnetic gradients at the agents.

In one embodiment, the one or more magnets have dimensions that substantially match the distance from the magnetic, magnetizable, or magnetically-responsive agents to the magnet, so as to maximize the strength of the magnetic gradient applied by the magnet to the magnetic, magnetizable, or magnetically responsive agents. In some embodiments, the one or more magnets have a length, width and height of from about 1 mm to about 10 cm, from about 3 mm to about 7.5 cm, from about 5 mm to about 2.5 cm, and from about 5 mm to about 1 cm. In some embodiments, the length, width and height dimensions are all the same, while in other embodiments, the length, width and height dimensions are different or at least some of the dimensions are different.

In some embodiments, the externally applied magnetic field is achieved with a Halbach array, which is a special arrangement of permanent magnets that augments the magnetic field on one side of the array while cancelling the field to near zero on the other side. In some embodiments, this can be achieved by having a spatially rotating pattern of magnetisation.

The magnet shape is not particularly limiting. In some embodiments, the shape of the magnet maximizes magnetic gradients (e.g., has sharp corners). In some embodiments, the magnet shape is selected to roughly match the shape/size of a tooth or jaw, whether placed inside or outside the mouth. In some embodiments, the shape of the magnetic system could be chosen to fit around the bottom jaw of the patient, to allow magnets inside the system to be as close as possible to the teeth that would be treated. The system could be designed to fit around the jaw for one tooth (e.g. an L shape that would be placed under that tooth), or it could be designed to provide forces for all teeth at once (e.g. a horseshoe shape that would fit under the lower jaw to provide pull-in forces for all teeth in the lower jaw). For the upper teeth, to optimally provide pull forces, the magnetic system could be shaped so that it lies above or next to the cheek bones, in order to be as close as possible to the upper teeth and provide effective pull-up into the teeth magnetic forces. One knowledgeable in the art would recognize that the shape of the magnets and/or magnetic elements inside the system could further be chosen to provide optimal forces. Linear optimization methods, or other standard programming optimization methods, could be used to select the size, shape, and magnetization direction for the magnets or magnetic elements inside the system, to cause magnets or magnetic element to act together in concert so that the strength of magnetic forces on the agents are maximized, and so that the direction of forces is optimal over the desired area. In some embodiments, the magnetic field is optimized using finite element analysis and magnetic modeling to optimize magnet placement, so as to have a steep, substantially uniform or optimized magnetic gradient over a specific region in space corresponding to a region of interest in the tooth or periodontium.

It is further understood that different patients will have different jaw sizes, shapes, and teeth orientations, and the magnetic system can be adjustable so that magnetic forces can be tuned on a per patient bases for optimal delivery of the agents to targets in, under, above, or around the teeth. The number of magnets could range from just one to many, for instance up to two, five or ten magnets per tooth. Thus a full jaw magnet may have as many as tens of individual magnets whose placement, shape, orientation and magnetization is chosen so as to create the desired forces on the agents. In some embodiments, one or more magnets are positioned inside the oral cavity. In some embodiments, one or more magnets are positioned outside the oral cavity. In some embodiments, one or more magnets are positioned inside the oral cavity and one or more magnets are positioned outside the oral cavity to achieve the desired magnetic field.

In some embodiments, magnets are constructed out of materials such as iron, cobalt, nickel or combinations of these materials and can include rare-earth compound materials such as neodymium and samarium-cobalt as well as other materials known to those skilled in the art. In some embodiments, the external magnetic field is provided by one or more neodymium magnets. A neodymium magnet (also known as NdFeB, NIB or Neo magnet) is a permanent magnet made from an alloy of neodymium, iron and boron to form the Nd2Fe14B tetragonal crystalline structure. In some embodiments, the external magnetic field is provided by one or more iron-based magnets, neodymium-iron-boron-based magnets, samarium-cobalt-based magnets, any other rare-earth (such as lanthanoid) based magnet and combinations thereof. Magnets can be obtained commercially. Such magnets are available from K&J Magnetics (Pipersville, PA).

In some embodiments, a small magnet can be applied extraorally under the jaw to apply magnetic forces to the mandibular (lower) teeth. In some embodiments, it can be placed extraorally, on the check, adjacent to maxillary tooth roots to apply magnetic forces to maxillary (upper) teeth. In some embodiments, more appreciable forces on the agents can be applied if magnetic arrays are employed that would create a strong magnetic gradient, rather than a locally uniform magnetic field. Such a magnetic array is shown in FIG. 6.

Figure 7:
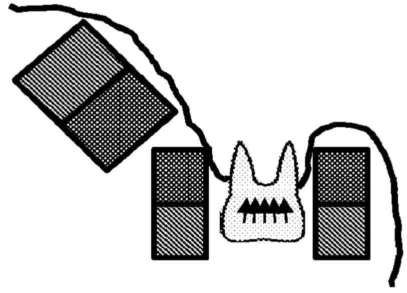
FIG. 7. A design of intraoral magnetic arrays that can be used to apply a magnetic field to steer nanoparticles into dentinal tubules. In this example, 3 small magnets are used.

In addition to extraoral designs, magnetic arrays can be applied intraorally. One examples of such design is shown in FIG. 7. In some embodiments, intraoral devices can be retained in the mouth using a resin appliance (e.g.: retainers, occlusal devices).

In some embodiments, the external magnetic field is achieved by one or more magnets that are positioned in a way that applies a pulling force on the magnetic, magnetizable, or magnetically responsive agents. Orientations of magnets that apply a pulling force are shown in FIGS. 6, 7, 9, 10, 11, 12, and 13.

Figure 6:
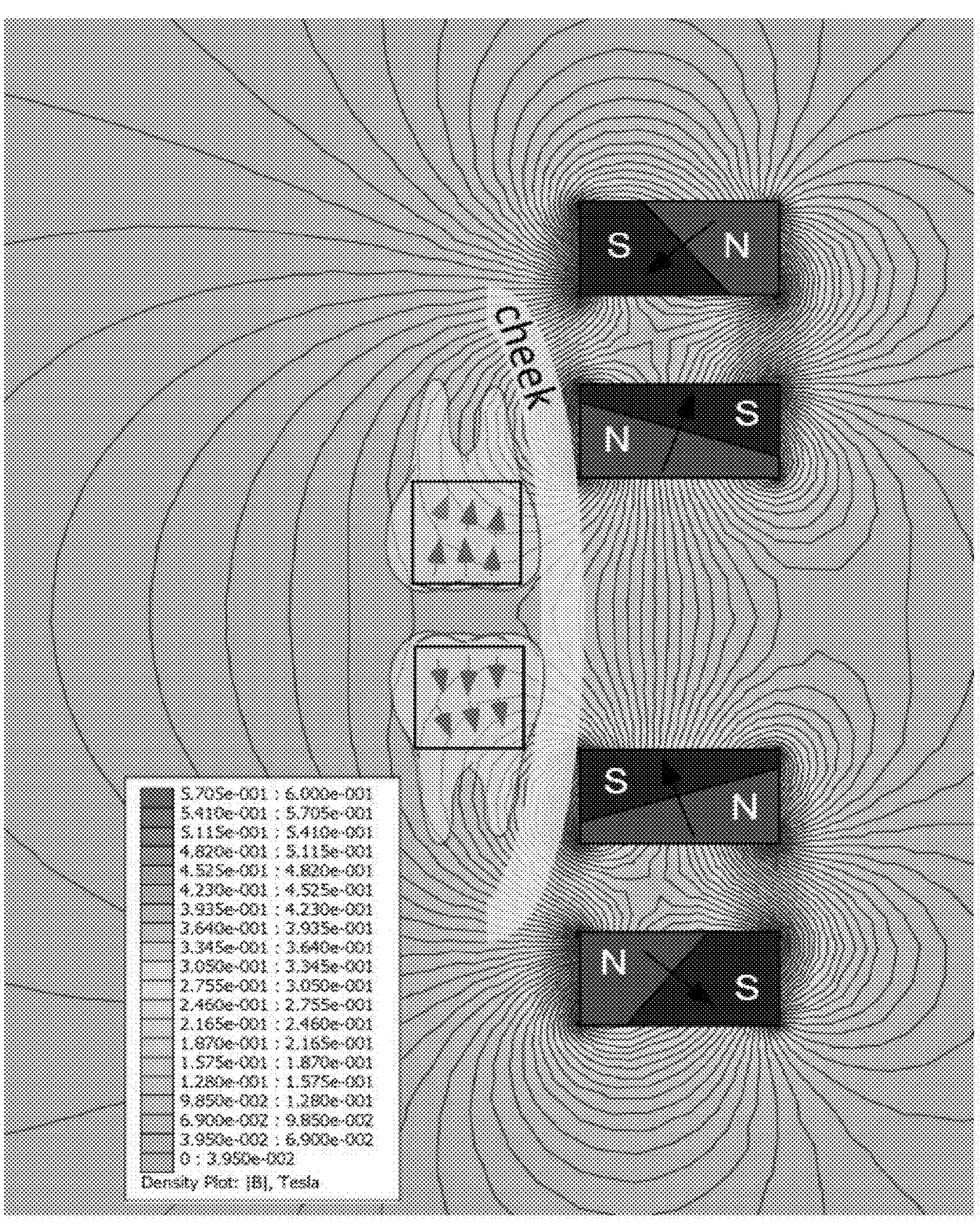
FIG. 6. Custom made array made of 4 Neodymium N52 magnets (N=north pole of the magnet, S=south) for application of nanoparticles to maxillary teeth. To design this array, "Finite Element Method Magnetics" was used to compute the magnetic field and used Matlab for optimization. This allowed optimization of the direction and magnitude of forces on the particles (arrows). Linear optimization was performed along a line 1.5 cm away from the face of the array. Standard optimization techniques can be used to create maximal and uniform forces over a wider distance, using a variable number and size of magnets and different magnetic field strengths. This configuration allows pulling nanoparticles apically in maxillary teeth, and mandibular teeth if necessary. Black lines represent magnetic fields. The forces are shown by the arrows inside the two teeth.

FIG. 6 shows an embodiment of an array made of 4 neodynium N52 magnets (N=north pole of the magnet, S=south) for application of nanoparticles to maxillary teeth is shown. To design this array, "Finite Element Method Magnetics" was used to compute the magnetic field and Matlab was used for optimization. C. Meeker, Finite Element Method Magnetics, Version 4.0.1 (3 Dec. 2006 Build), http://www.femm.info. This allowed optimization of the direction and magnitude of forces on the particles (arrows). Linear optimization was performed along a line 1.5 cm away from the face of the array. This optimization technique can be used to create maximal and uniform forces over a wider distance, using a variable number and size of magnets and different magnetic field strengths. This configuration allows a pulling of the nanoparticles apically in maxillary teeth, and mandibular teeth if necessary. Black lines represent magnetic fields.

In some embodiments, three magnets positioned intraorally can be used to apply a magnetic field to steer nanoparticles into dentinal tubules. An exemplary embodiment is shown in FIG. 7.

Figure 9:
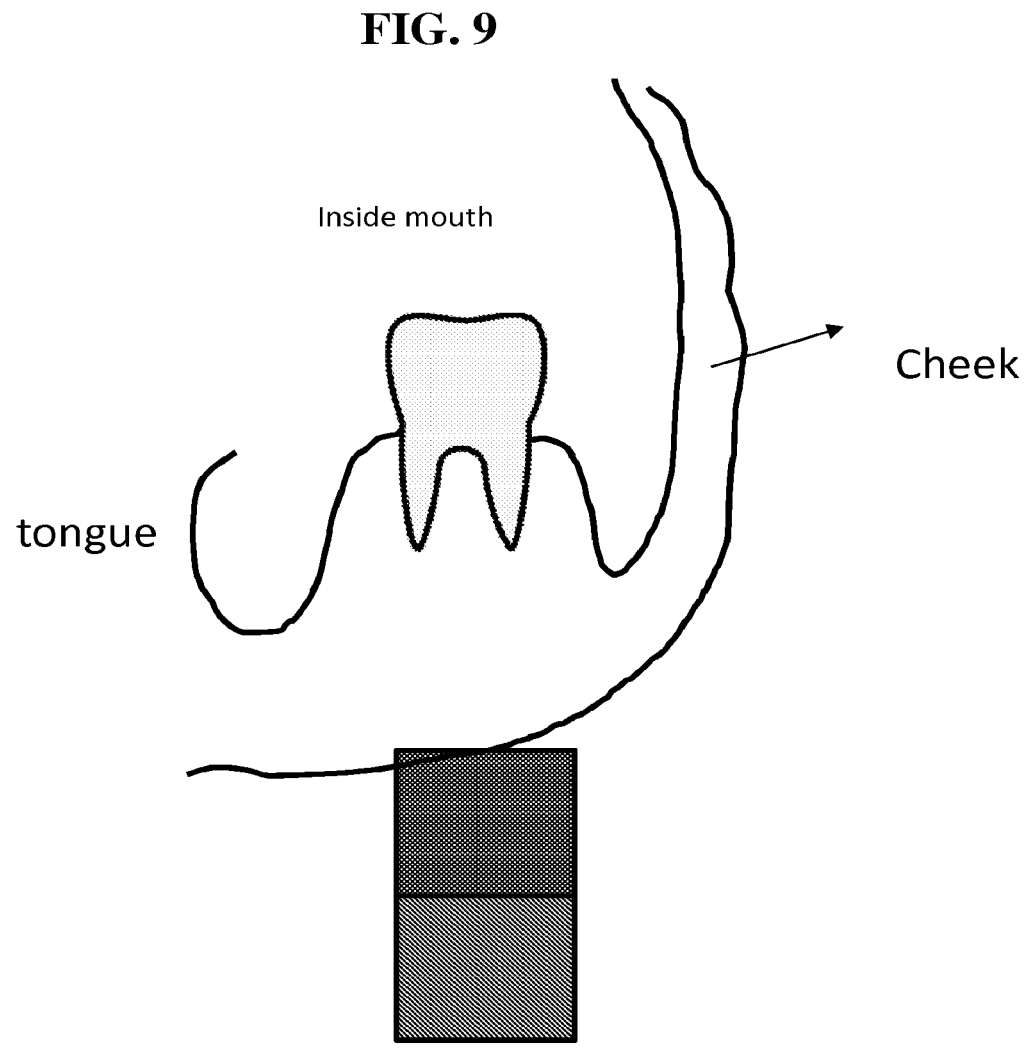

In some embodiments for treating lower teeth, a single magnet or multiple magnets can be placed in parallel, placed under the mandible, and right under the tooth to be treated. This embodiment is shown in FIG. 9. In some embodiments, the magnet can be placed inside a holder to keep its position fixed with respect to the base of the mandible.

Figure 10:
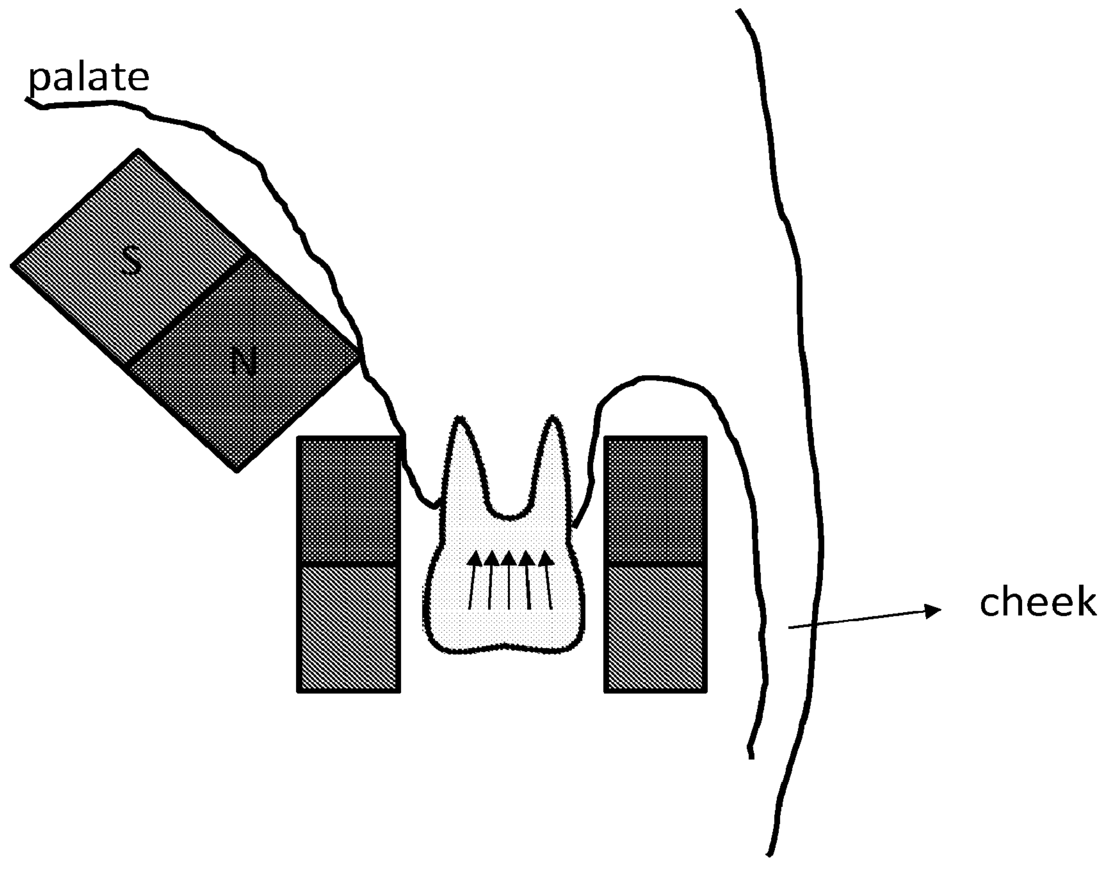
FIG. 10. One embodiment of a configuration of magnets for delivering agents to the upper teeth. For the upper teeth, a system with 3 magnets or combinations of magnets with the general orientation shown will generate a magnetic pull force that is relatively uniform over the dentinal portion of the tooth. Two thin magnets sit on either side of the tooth, with a third, stronger magnet placed at an angle against the palate. The "thin" magnets only have to be thin enough so one can be placed between cheek and tooth. The magnets will have to be placed within a holder to keep their relative position fixed with respect to each other. The holder will be designed so as to remain fixed and well positioned with respect to the maxillary tooth. This design is useable for the lower teeth as well.
Figure 11:
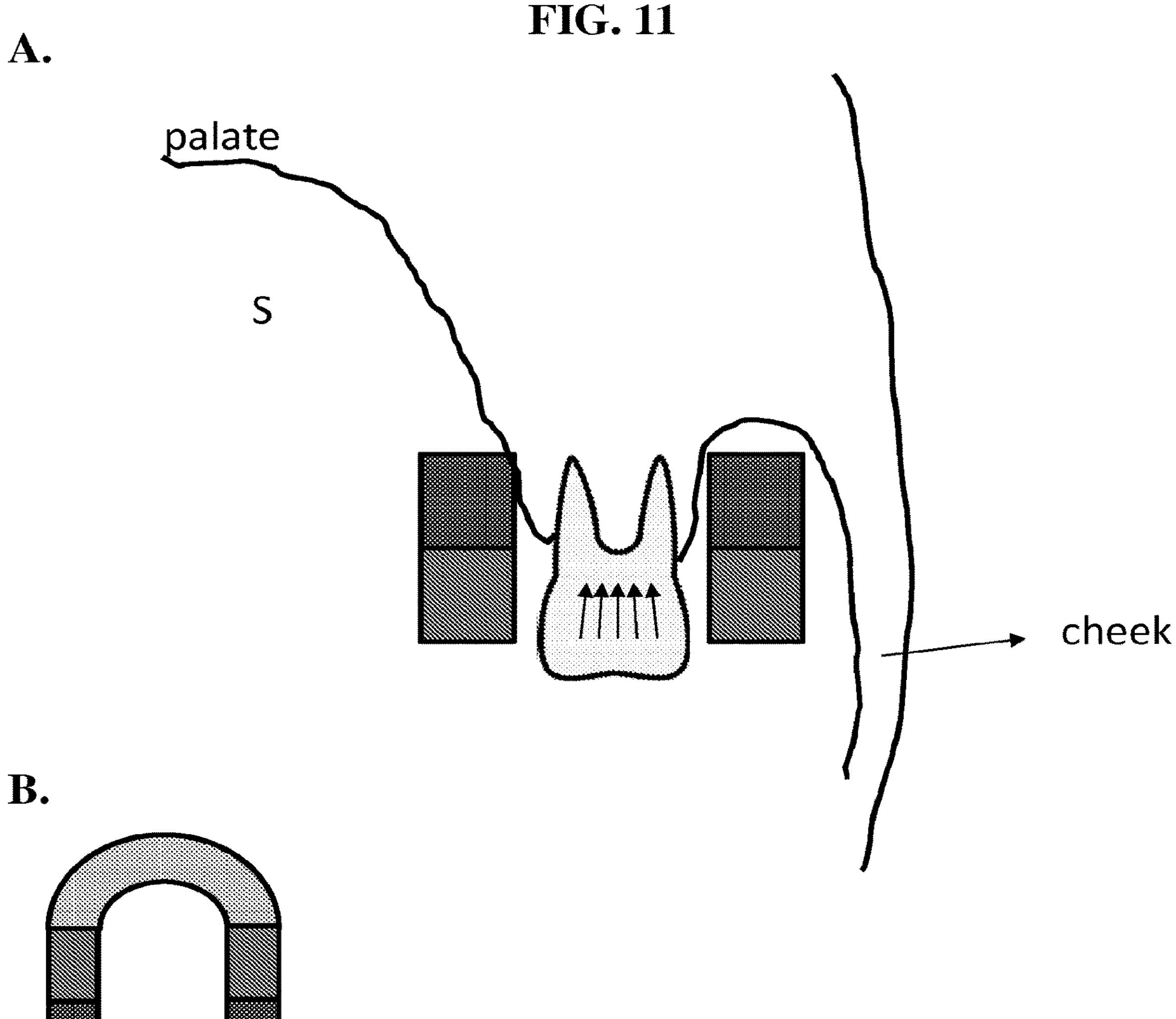
FIG. 11. (A) An embodiment for treating upper and lower teeth with two magnets (or combinations) of magnets with the general orientation shown will generate a magnetic pull force over the dentinal portion of the tooth. Two magnets can sit on either side of the tooth. The center of the magnet should be aligned with the pulp. This will create a magnetic pull force from the line that connects the ends of the magnets (for instance, the lower end of the lighter colored region) to a line connecting the centers of the magnets. The magnets only have to be thin enough so one can be placed between cheek and tooth. (B) An example of a holder for the magnets. The magnets will have to be placed within a holder to keep their relative position fixed with respect to each other. The holder will be designed so as to remain fixed and well positioned with respect to the maxillary tooth. In other words, the system might look like the horseshoe shown at the bottom right. This design is useable for upper and lower teeth.

In some embodiments for treating upper teeth, a system with 3 magnets or combinations of magnets with the general orientation shown in FIG. 10 will generate a magnetic pull force that is substantially uniform over the dentinal portion of the tooth. In this embodiment, two thin magnets are sitting on either side of the tooth, with a third, stronger magnet placed at an angle against the palate. The "thin" magnets only have to be thin enough so one can be placed between cheek and tooth. The magnets can be placed within a holder to keep their relative position fixed with respect to each other. The holder can be designed so as to remain fixed and well positioned with respect to the maxillary tooth. This design is also useable for the lower teeth, except that the larger magnet would be placed under the tongue.

In some embodiments where it is desired to treat the upper and lower teeth, two magnets or combinations of magnets with the general orientation shown in FIG. 11A will generate a magnetic pull force over the dentinal portion of the tooth. In this embodiment, two magnets sit on either side of the tooth. The center of the magnet should be aligned with the pulp. This will create a magnetic pull force from the line that connects the ends of the magnets (for instance, the lower end of the lighter colored region) to a line connecting the centers of the magnets. In some embodiments, the magnets only have to be thin enough so one can be placed between cheek and tooth. In some embodiments, the magnets will have to be placed within a holder to keep their relative position fixed with respect to each other. The holder will be designed so as to remain fixed and well positioned with respect to the maxillary tooth. In some embodiments, the system would resemble a horseshoe shape shown in FIG. 11B.

Figure 12:
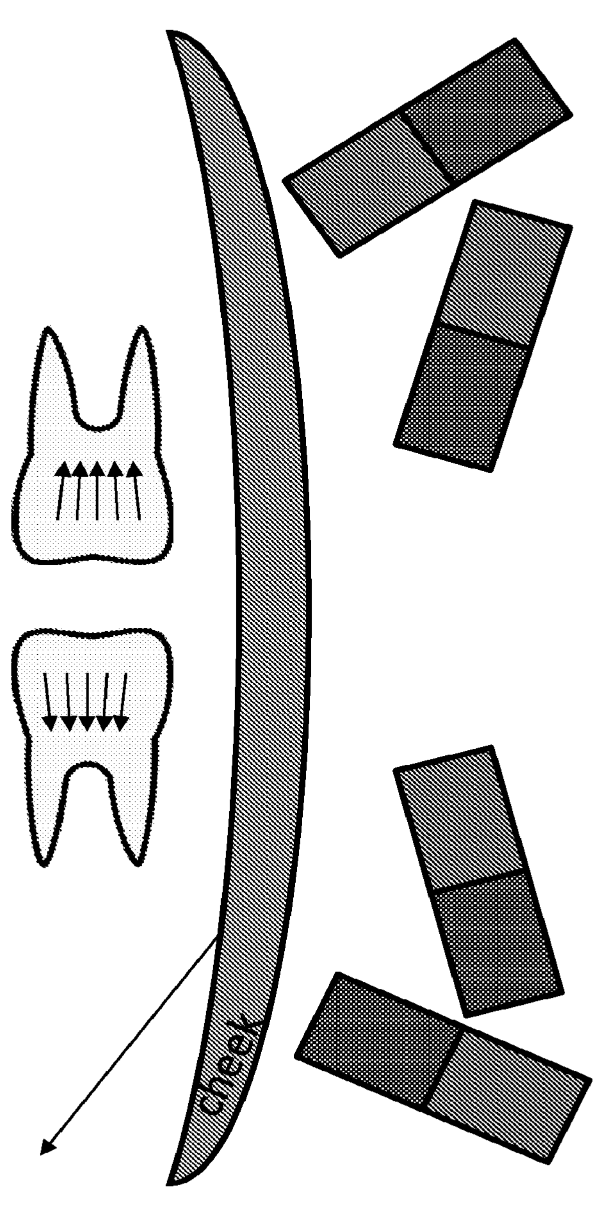
FIG. 12. For a system that works for both upper teeth and lower teeth, while staying outside the body, the schematic shown provides a uniform, upward magnetic force for upper teeth and downward magnetic force for lower teeth. The alignment between the position of the magnet array, (outside the mouth and against the cheeks), and the teeth inside can be accomplished either with landmarks, or with a horizontal U-shaped piece, with one side of the U holding the magnet array, and the other side of the U inside the mouth, with the patient biting lightly on that second part of the piece to assure alignment of the magnet array with the teeth. Note that using only the upper 2 magnets will provide a magnetic force only within the upper teeth. Similarly, using only the lower 2 magnets will provide a magnetic force only within the lower teeth. While one needs to provide at least 2 magnets to provide a magnetic force along the long axis of the dentinal tubules, (the reader familiar with the design of Hallbach arrays will easily understand that) similar designs can be obtained with 3, 4, magnets with intermediate orientations to those illustrated here.

In some embodiments, the one or more magnets can be configured to treat both upper and lower teeth while staying outside the oral cavity, as shown in FIG. 12. In this embodiment, the arrangement of magnets will provide a uniform, upward magnetic force for upper teeth and downward magnetic force for lower teeth. The alignment between the position of the magnet array, (outside the mouth and against the cheeks), and the teeth inside can be accomplished either with landmarks, or with a horizontal U-shaped piece, with one side of the U holding the magnet array, and the other side of the U inside the mouth, with the patient biting lightly on that second part of the piece to assure alignment of the magnet array with the teeth. In this embodiment, the upper 2 magnets will only provide a force only on the upper teeth. Similarly, the lower 2 magnets will only provide a force on the lower teeth. While in some embodiments, one needs to provide at least 2 magnets to provide a magnetic force along the long axis of the dentinal tubules, similar designs can be obtained with 3, 4, 5, 6, etc., magnets with intermediate orientations to those illustrated here.

Figure 13:
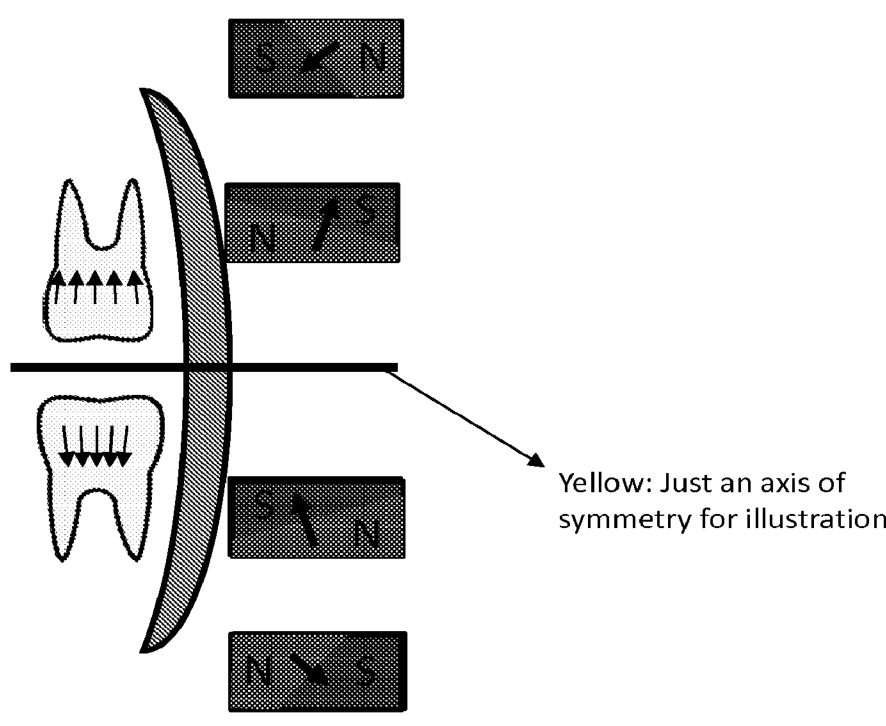
FIG. 13. Standard cuboid shaped magnets, with the magnetization not along one of the main axes of the cuboid, but an optimally chosen axis.

In another embodiment, as shown in FIG. 13, standard cuboid shaped magnets can be used, with the magnetization not along one of the main axes of the cuboid, but an optimally chosen axis. In some embodiments, more complex arrays are can be designed with a higher number of magnets with intermediate orientations. The magnet array that results in a magnetic pull force along the arrays shown within the teeth in FIG. 13 will repeal each other if free to move or rotate, so it is understood that the magnets (and especially the orientation of their magnetization) are to be held in a non-magnetic device.

The externally applied magnetic field is applied for a period of time in order to achieve the migration of the magnetic, magnetizable, or magnetically-responsive agents to the desired location in the tooth or periodontium. In some embodiments, the externally applied magnetic field is applied for about 30 seconds to about 120 minutes. In some embodiments, the externally applied magnetic field is applied for about 30 seconds, about 60 seconds, about 2 minutes, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, or longer.

The magnets can be positioned and held into position while the force is applied. In some embodiments, the one or more magnets are held in the proper configuration using one or more holding devices. In some embodiments, the one or more magnets are held into position using a mouthpiece. In some embodiments, the holding device is a retainer. In some embodiments, the subject is asked to bite down on an object which is attached, either directly or indirectly, to one or more magnets and which holds the magnet(s) in the proper configuration.

While the embodiments have been described with reference to certain particular examples and embodiments herein, those skilled in the art will appreciate that various examples and embodiments can be combined for the purpose of complying with all relevant patent laws (e.g., methods described in specific examples can be used to describe particular aspects of the embodiments and its operation even though such are not explicitly set forth in reference thereto).

Aspects of the present teachings may be further understood in light of the following examples, which should not be construed as limiting the scope of the present teachings in any way.

EXAMPLES

Example 1

Figure 2:
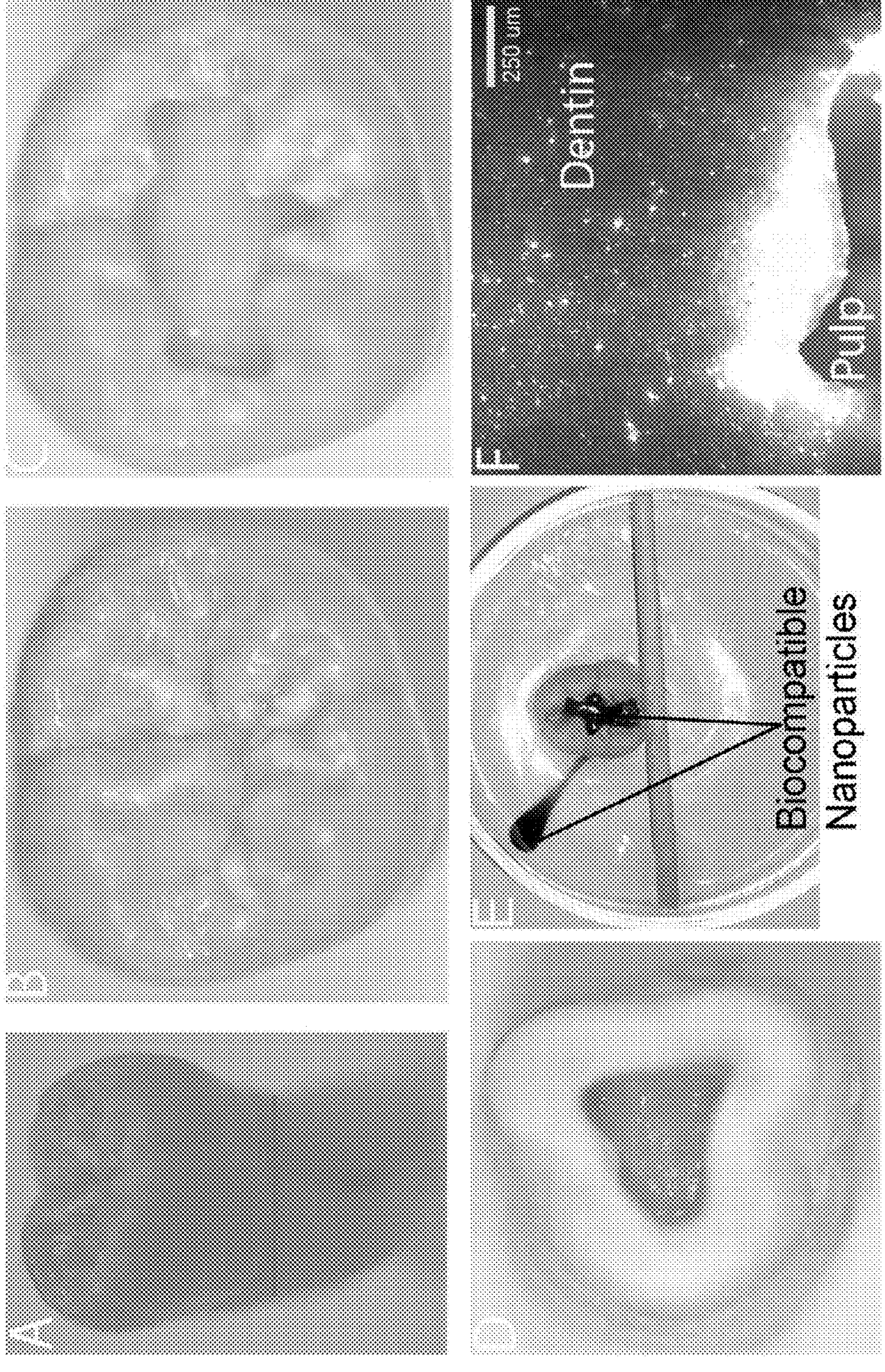
FIG. 2. Experimental design and delivery of nanoparticles to the pulp. (A) An example of a molar tooth with intact crown and root. (B) Birds-eye view of the tooth showing the occlusal surface. (C) Cavity preparation exposing the dentin of the tooth without affecting the integrity of the pulp. (D) The apical (bottom) view of the same tooth after sectioning at the level of the pulp chamber (line in A) to test if nanoparticles pass from the dentin to the pulp chamber. (E) Nanoparticles (300 nm hydrodynamic diameter) applied to the cavity pass through dentin to the pulp (a magnet is positioned under the dish). (F) A longitudinal section in a tooth treated with nanoparticles (300 nm). Epi-fluorescence microscopy (10×) reveals that Nanoparticles (white) penetrate deep into dentinal tubules, passing through secondary dentin (formed after tooth eruption), before reaching the pulp.

Initial experiments were performed to test if nanoparticles can be guided to the tooth pulp chamber through dentinal tubules using magnetic forces. To this end, freshly extracted molar teeth were obtained (FIG. 2A) from the oral maxillofacial surgery clinics at the University of Maryland, Baltimore. The teeth were cleaned with a toothbrush and a disinfecting solution (5.25% sodium hypochlorite). The distance between the occlusal surface (biting surface) of the teeth (FIG. 2B) and the pulp was measured before preparing a cavity (FIG. 2C) to simulate dental decay and to expose the dentin. This cavity preparation is typical of treatment routinely performed by dentists to remove decay before placing a filling. The depth of the cavity was on average 2 mm. The teeth were sectioned horizontally at the level of the pulp chamber using a diamond disk (FIG. 2D; line in 2A). The teeth were suspended in saline, in a petri dish, and placed on top of a magnet. Nanoparticles (50 μL) of 100, 300 and 500 nm hydrodynamic size, were placed in the cavity. The particles have a magnetic core that allows them to be steered, in this case pulling them to the magnet. After 30 minutes, nanoparticles can be seen in the petri dish under the teeth, an example is shown in FIG. 2E. Teeth were then sectioned longitudinally and examined under an epi-fluorescence microscope. Fluorescent nanoparticles reach the pulp chamber and can be seen penetrating deep into dentinal tubules (FIG. 2F, see also FIG. 4C). This experiment was performed on 9 teeth and similar results were obtained throughout. Depending on particle diameter and duration of the magnetic forces, particles were not always seen in the dish under the tooth, but in all cases, particles were seen at least in the pulp horns (FIG. 2F, see also FIG. 4C). In addition, inductively coupled plasma atomic emission spectroscopy (ICP-AES) was used to quantify the amount of nanoparticles delivered through dentinal tubules. In the tooth shown in FIG. 2, 557 million particles were delivered for a drug equivalent of 320 ng (if for example, prednisolone eluting particles were used). In control experiments, when nanoparticles were applied to the tooth for 30 minutes without magnetic pull, nanoparticles were not seen in the saline under the teeth.

Figure 3:
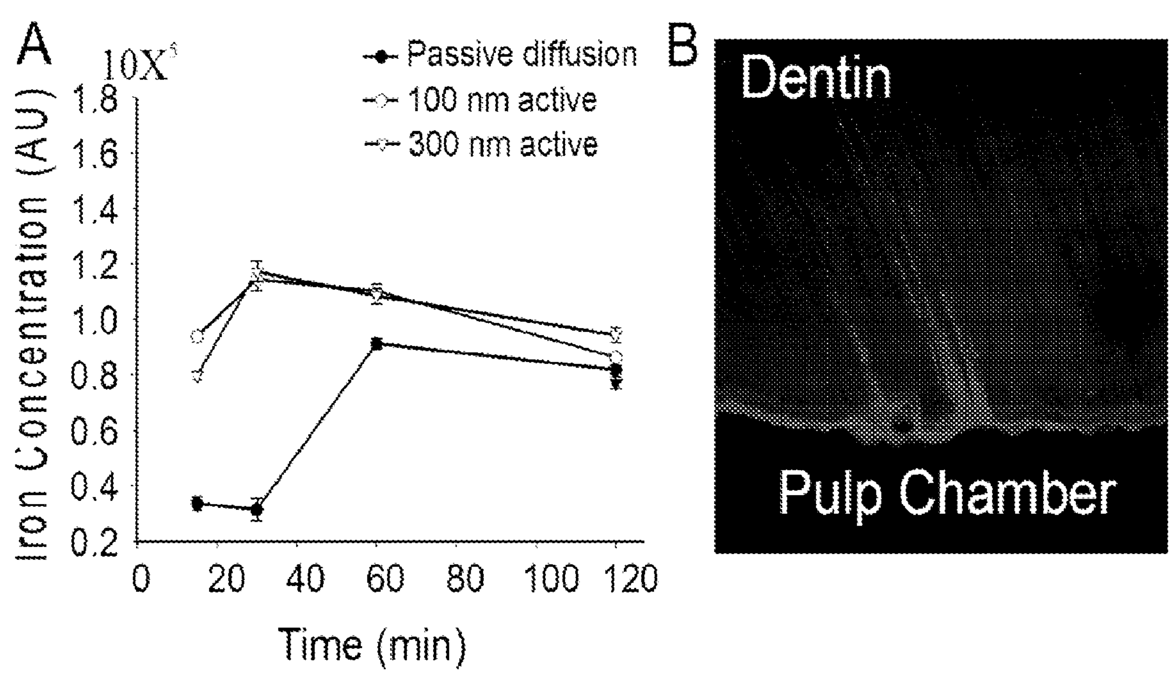
FIG. 3. Magneto-dynamics of nanoparticles guided to the pulp. (A) Chitosan-coated nanoparticles (100, 300 nm) and a magnet (1.4 T) were used to perform active pull. In passive experiments, the nanoparticles were placed in the prepared cavity and allowed to passively diffuse. Ninety-six teeth were used in these experiments. (B) A cross section of a tooth treated with 300 nm nanoparticles and viewed using confocal microscopy (20×) is shown. Notice the nanoparticles in dentinal tubules and reaching the pulp chamber.

FIG. 3 provides a summary of results. Nanoparticles in the range of 100-300 nm are delivered efficiently to the tooth pulp in a short time, compared to passive diffusion. There was no difference in the amount delivered between larger particles (300 nm) and smaller particles (100 nm) (FIG. 3A). Nanoparticles reached the pulp fairly quickly (within 15 minutes of application) and reached a peak at 30 minutes (FIG. 3A). This is approximately the same amount of time a dentist needs to perform a restorative procedure on a tooth.

The following methods for in vitro testing in human teeth were used.

1—Obtained freshly extracted third molar teeth
2—The teeth were cleaned with a toothbrush and a disinfecting solution (5.25% sodium hypochlorite).
3—X-rays were used to measure the distance between the occlusal surface (biting surface) of the teeth and the pulp.
4—A cavity was prepared (2-3 mm deep) to simulate dental decay and to expose the dentin. This cavity preparation is typical of treatment routinely performed by dentists to remove decay before placing a filling.
5—The were sectioned teeth horizontally at the level of the pulp chamber using a diamond disk
6—The teeth were suspended in saline, in a petri dish, and place on top of an 1.2 Tesla neodymium magnet.
7—Nanoparticles were applied directly into the prepared cavity using a syringe or a microbrush.
8—The nanoparticles were collected that seep through dentinal tubules and quantify iron/drug quantity.
9—The tooth was sectioned and examined under confocal and electron microscopy.

Tooth Preparation

Human teeth. Extracted human teeth were obtained, disinfected, and stored in isotonic saline. An X-ray of each tooth was obtained before any preparation was performed. A carbide round bur (1 mm in diameter) attached to a high speed dental hand piece and copious irrigation was used to prepare a class I cavity in the tooth, extending 1 mm into the dentin. After preparation, another X-ray was taken and the thickness of the dentin measured. In addition, a diamond disk was used to cut the tooth at a level below the pulp chamber (FIG. 2).

Inductively coupled plasma atomic emission spectroscopy (ICP-AES). The tooth was sectioned into 2 mm thick sections and dissolved in 70% nitric acid for 24 h to dissolve the hydroxyapatite and the coating of the nanoparticle. The resulting material was filtered and run in our ICP-AES machine (Perkin Elmer Optima 4300 DV). The lower limit of quantification of iron using ICP-AES is 2 pg/2 mL. The measurements obtained from the samples were plotted against a standard curve to quantify the amount of nanoparticles in each sample. The distribution of particles, as a function of tooth preparation parameter (for instance, dentinal depth), was then determined.

Example 2

In addition to treating the inflamed dental pulp, the technology can be used to strengthen the bond of contemporary filling materials to dentin and reduce their polymerization shrinkage. The material of choice for filling tooth cavities is composite resin. Lynch et al., *J Dent.* 2014; 42 (4):377-383. Composite resins are relatively strong, esthetic and bond well to enamel. However, they do not bond well to dentin (the tooth layer compromising the majority of the area to be filled) and they shrink considerably once they polymerize. Malhotra et al., *Compend Contin Educ Dent.* 2011; 32 (5):14-23; quiz 24, 381 Drummond J L., *J. Dent Res.* 2008; 87 (8):710-719.

Figure 8:
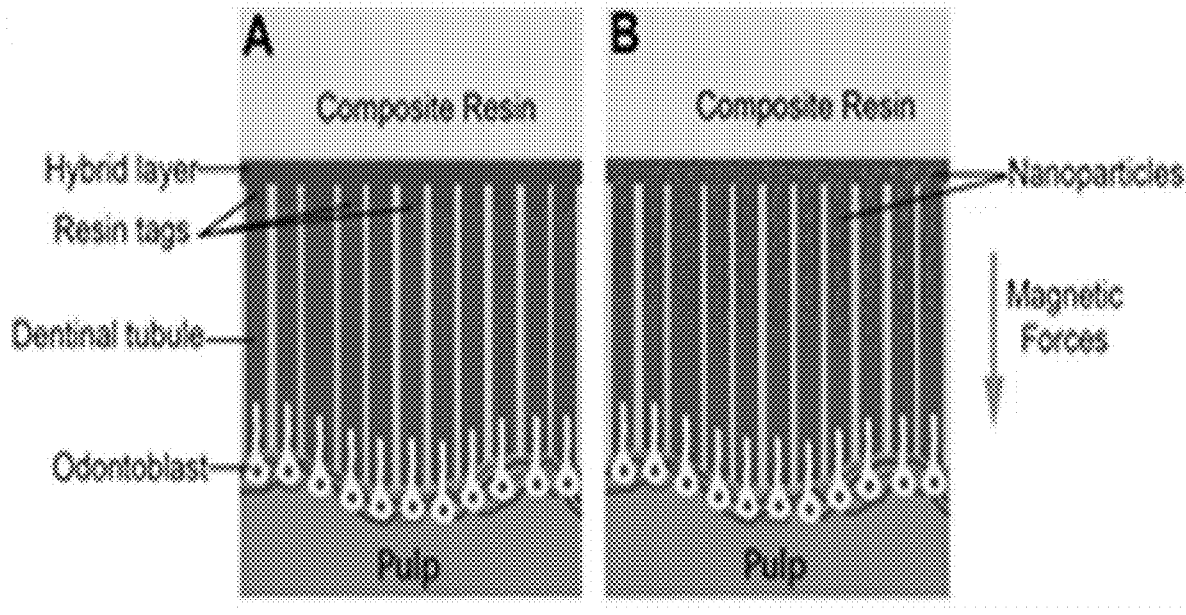
FIG. 8. (A) A cartoon of a longitudinal section in the dentin of a tooth restored with composite resin representing the current standard of care. Resin bonding agent is applied to the dentin and composite resin binds to the bonding agent forming a hybrid layer. The filling is retained through the passive formation of resin tags in dentinal tubules. (B) By applying magnetic forces to actively and deeply introduce magnetic nanoparticles coated with bonding agent into dentinal tubules, it allows formation of more retentive resin tags. This will significantly increase the surface area of dentin available for bonding, counteract polymerization shrinkage, and improve bond strength.

Poor bonding to dentin and polymerization shrinkage result in poor adaptability of the filling to the tooth, poor seal and microleakage and the development of recurrent decay and pulpitis. Ultimately, this will reduce the longevity of the restoration. Ballal N V., *Aust Dent J.* 2008; 53 (4):369; author reply 369-369; author reply 370; Li et al., *Dent Mater.* 2009; 25 (5):582-588; Goldstein G R., *J. Evid Based Dent Pract.* 2010; 10 (1):30-31. Magnetic forces and magnetic nanoparticles (500-900 nm) will be used to actively steer dentin bonding agents deeper into dentinal tubules of freshly extracted human teeth (FIG. 8). This will allow an increase in the surface area of dentin available for bonding and to counteract polymerization shrinkage of dental restorations.

Example 3

This Example describes use of nanoparticles and magnets to increase the bond strength of dental restorative materials and cements to tooth structures.

Figure 5:
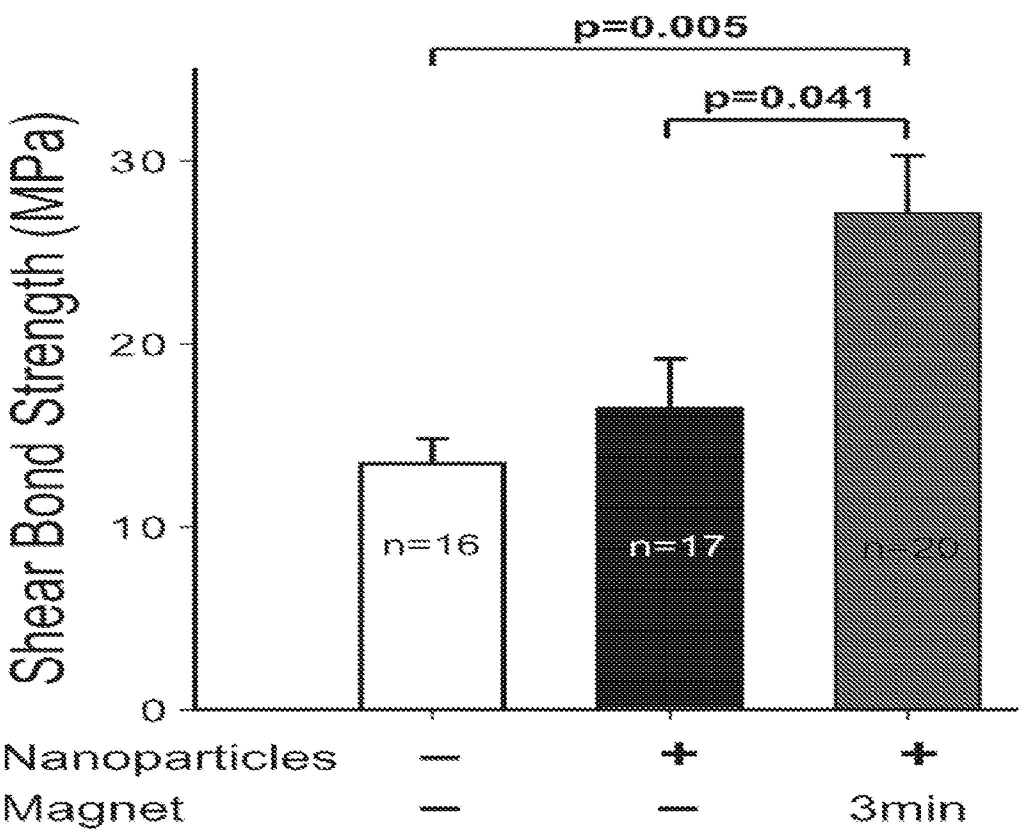
FIG. 5. Nanoparticles that are mixed with dentin bonding agent and magnetically steered into dentinal tubules doubled the shear bond strength of composite restorations.

Because contemporary dental restorations and cements rely on micromechanical retention using dentinal tubules, it was tested whether the technology can improve the shear bond strength of composite resin (esthetic dental filling) to dentin-a significant clinical problem in the field of restorative dentistry. The nanoparticles (1000 nm) were mixed with composite bonding agents (available commercially) and a magnet was used to pull the bonding agent into dentinal tubules for a period of 3 minutes. It was found that this method doubles the shear bond strength of composite compared to controls (unmodified bonding agent and no magnetic force) and in controls with modified bonding agent and no magnetic force (FIG. 5).

The following protocols were used in this example.

Protocol for Testing Shear Bond Strength

TEETH COLLECTION (Human Non-Carious-3 Molars)

1—Clean the teeth and remove periodontal tissue
2—Keep the teeth in thymol solution in cold refrigeration at 4° C.
3—Remove from solution immediately before use.
4—Use long tweezers to do it.

Teeth Preparation

1—Prepare acrylic resin with exact proportions of power and liquid to measure out the mixing of the two parts (used brand: Jet Acrylic).
2—Place the resin in the acrylic cylinder cup.
3—Insert the tooth inside the resin up to the enamel-dentin junction or 3-4 mm outside the cylinder.
4—When the resin cures, check around the tooth and fill the voids.
5—Identify your sample by tag or writing on the bottom.
6—Cut using a low speed saw machine. First place a diamond wafering blade in the machine. Try to place the tooth perpendicul to the saw. Ensure that the tooth is well-fixed. Make a marking in the crown 4 to 5 mm from the enamel-dentin junction so that the cut does not expose the pulp chamber. Add some micromechanically retention around the root using a low speed diamond disc.
7—Grind the tooth to expose flat dentin surface and to standardize the smear layer. First, place sandpaper #600 on the grinder. Placer your sample in central fixed-machine plastic gutter device. Apply moderate strength. Use the dissecting microscope to make sure that the midcoronal dentin is exposed. Keep the teeth in distilled water at cold room Nanoparticle-Adhesive Preparation 1—Weigh nanoparticle and add desired dentin bonding adhesive to establish a 30% solution of nanoparticles. Place the mixture in ultrasonic device for 15 minutes. After sonication, the nanoparticle/adhesive solution is ready to use.
2—To prepare nanoparticles coated with silane coupling agent. Add silane to nanoparticles and make sure all nanoparticles are covered. Sonicate for 15 minutes. Place on a shaker with heat for 30 minutes and allow the nanoparticles to dehydrate. Once dehydrated, the particles are ready for use.

Bonding Procedures

1—All the adhesive procedures should be done at yellow light room to avoid premature light cure of the resin-based material
2—Remove the teeth from water; grinding procedure should be done just before (30 min) the adhesive procedures.
3—Keep a humid towel over the samples
4—Dry the excess water over the flat dentin area
5—Apply the etching acid for 15 s (35% phosphoric acid).
6—Rinse for 10 seconds. Remove excess water using light air. The surface should appear glistening without pooling of water.
7—Apply 1 coat of primer with gentle agitation using a fully saturated applicator, gently air thin for 1-2 seconds.
8—Apply 1 coat of nanoparticle-adhesive solution with gentle agitation using a fully saturated microbrush. Gently air thin for 2-3 seconds to evaporate the solvents.
9—Light cure for 10 seconds.

Restorative Procedures

1—Perform a 6-mm-high buildup of composite resin, (Filtek Z250 (3M ESPE), shade A3) (* it is important use the same type of composite for all samples). Apply composite in 3 increments, and polymerize each for 20 seconds.
2—Keep 5 min in room temperature for cooling after the exothermic polymerization of the monomers, then keep in distilled water for 24 h in room temperature before the test.

Microtensile Bond Strength Test

1—Place the sample in a holding device on the INSTRON machine.
2—Open the INSTRON software. Insert the following parameters: number of samples, width and thickness/diameter.
3—Crosshead speed of 0.5 mm/min
4—Perform test.
5—The first test should be done for calibration, without the sample.
6—Save all data in a folder on the computer.

Example 4

This Example describes a method of delivering nanoparticles to the pulp using magnetic forces using human teeth in a patient.

1—Place rubber dam to isolate the tooth and avoid contamination from saliva in the oral cavity 2—Prepare the tooth to remove decay using carbide burs.
3—Rinse the tooth thoroughly with a water jet
4—Dry the tooth gently
5—Apply etching solution (35% phosphoric acid) for 15 seconds to remove smear layer from dentin surface
6—Apply drug-eluting nanoparticles to the prepared cavity using a syringe or a microbrush.
7—Apply magnetic device under the chin, next to the cheek or intraorally, based on the optimum design desired and tooth location. Apply magnetic forces for 30 minutes.
8—Rinse the tooth and restore using conventional restorative dentistry.

Example 5

Figure 4:
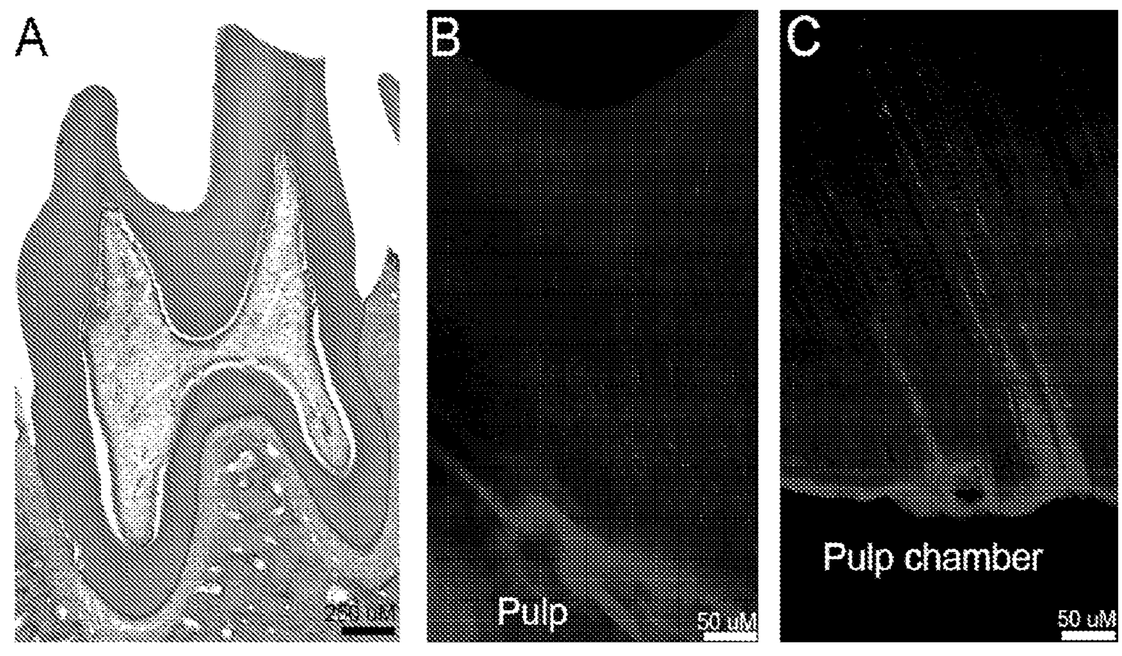
FIG. 4. A decalcified section of a rat molar tooth treated with nanoparticles and stained with H&E is shown (magnification: 4×). (B) An adjacent, unstained, section from the same tooth was viewed using a fluorescent microscope at 20×. Nanoparticles penetrate deep into dentinal tubules and are present in pulpal tissues. To perform this experiment, a cavity (0.25 mm deep and 0.5 mm diameter) was prepared in the occlusal surface a rat mandibular left molar. Nanoparticles (300 nm, starch coated) were applied to the cavity, in vivo, and subjected to magnetic pull for 30 minutes. The rat was then perfused and the mandible decalcified and serially sectioned (7 μm). (C) A decalcified section in a human molar tooth, treated in vitro as described in FIG. 2 and observed under a fluorescent microscope (20×). Nanoparticles penetrate deep into dentinal tubules, reaching the pulp chamber.

The technology was also validated in experimental cavities prepared in animals. Magnetic forces were used to deliver nanoparticles through dentinal tubules to the pulp in rat molar teeth. These nanoparticles penetrated deep into dentinal tubules and were present in pulpal tissues as shown in FIG. 4. Based on histological examination, we have not observed any toxicity of these nanoparticles on pulpal tissues in these preliminary rat experiments (FIG. 4A).

The following methods were used in this example.

Methods for In Vivo Testing in Animal (Rat) Teeth:

1—Anesthetize animals
2—In each animal 4 mandibular molars were prepared for occlusal cavities, two on each side.
3—On the experimental side, nanoparticles were applied. On the other side no particles were applied.
4—The cavity size was approximately 0.25 mm deep and 0.5 mm in diameter and will only extend into the dentin, leaving the pulp chamber intact.
5—A magnet was placed under the mandible of the animals. After 30 min of exposure to magnetic forces, the teeth were washed thoroughly using sterile saline, then dried.
6—A light-cured composite resin restoration was used to fill the tooth using the same procedures performed in dental clinics.
7—The animals were sacrificed 1 week, 1 month, or 6 months after nanoparticle application.
8—To harvest the tissue, the animals were be euthanized.
9—The entire mandibular jaw was harvested and cut at the middle to separate the control side from the experimental side.
10—Each side was further divided into two parts, each containing one prepared molar tooth.

Detailed Methods:

Animal anesthesia and preparation. The animals were anesthetized using ketamine/xylazine (100/10 mg/kg, I.P.) or isoflurane (5% for induction and 1-3% for maintenance). The anesthetized animals were placed on a surgical table on top of a regulated heating blanket in the supine position. A small horizontal metal bar secured to the surgical table was placed on top of the mandibular incisors to stabilize the mandible. A stereotaxic incisor holder was attached to the maxillary incisors to open the mouth. A dissecting microscope was used to visualize the teeth during preparation.

Tooth Preparation.

Rat teeth. A high speed dental hand piece will be used to prepare rat mandibular molars. Irrigation with cold, sterile isotonic saline will be applied every 5 s during preparation to avoid excessive heat. Suction will be applied at the same time to prevent saline from penetrating the animal's airway. A round carbide bur will be used (0.4 mm in diameter). The cavity will extend either 0.25 mm into dentin or into the pulp. To extend the cavity into the pulp, minimal pressure will be exerted on the hand piece until the roof of the pulp chamber is penetrated.

Nanoparticle application in rats. A magnet (1.4 T) will be placed under the mandible of the rat, and nanoparticles (50 μL, >9 billion particles) will be applied to the cavity. After 30 min, the magnet will be removed and the cavity will be washed using isotonic saline and suction. Then the cavity will be etched using 37% phosphoric acid, bonding agent will be applied and light-cured, and composite will be applied and light cured. Finally, the restoration will be finished and polished to ensure that it conforms to the tooth contours and that it is not sharp or rough.

Euthanasia. The animals will be euthanized with sodium pentobarbital (100 mg/kg). We will perfuse the rats transcardially with buffered saline followed by 4% buffered paraformaldehyde. The mandibular jaw containing the teeth will be decalcified, embedded in paraffin, and 7 μm thick coronal sections will be cut.

H & E staining. The sections will be mounted on slides, deparaffinized, and cleared using xylene. Sections will be stained for 10 min with filtered 0.1% hematoxylin, then rinsed with distilled water. The sections will then be stained with eosin and dehydrated using alcohol. Mounting medium will be applied and the slides will be coverslipped before examination under the microscope.

Gram staining. Mounted sections will be deparaffinized and treated with xylene. The slides will be stained for 30 s using crystal violet oxalate, and rinsed. Sections will then be stained in iodine solution and rinsed. The sections will be decolorized using acetone-alcohol until the blue color stops running, then counterstained for 3 min with basic fuchsin stain (0.25%). The sections will be dipped in acetone, picric acid-acetone, and acetone-xylene solution (1:1) and cleared in xylene. Mounting media will be applied and slides will be coverslipped.

Histology. The part of the jaw including the prepared tooth will be decalcified using 4% EDTA, sectioned, and stained. Serial sections will be stained with hematoxylin and eosin (H & E), imaged using light microscopy, and analyzed using standardized histological criteria. The sections will be scored for the relative degree of inflammation, amount of fibrosis, presence of edema, condition of pulpal vessels, and odontoblastic integrity. The relative degree of inflammation will be graded as follows: no inflammation (0-2 infiltrating cells); light inflammation (2-5 infiltrating cells); moderate inflammation (5-10 infiltrating cells); or severe inflammation (>10 infiltrating cells). Fibrosis will be defined as an increase in fibroblast and collagen fiber concentration. The relative degree of fibrosis will be graded as follows: light fibrosis (3-10 fibroblast cells); moderate fibrosis (11-30 fibroblast cells); or severe fibrosis (≥31 fibroblast cells). The vessels will be categorized into three groups (normal, atrophied, or dilated), according to their size. The vessels will be classified as arterioles (thick-walled vessels with a diameter of 10-50 μm); venules (vessels with thin or absent muscular layers, with a diameter of 10-40 μm); capillaries (small vessels, usually with an undetectable lumen, and a diameter of 4-10 μm); or lymphatics (irregularly shaped vessels, 20-50 μm in diameter, and displaying numerous abluminal endothelial projections). Edema will be defined as the accumulation of interstitial fluids in pulp. In addition, we will measure the thickness of the periodontal ligament around each tooth; and the type of inflammatory cell infiltration in the pulp and around the root of the tooth (numbers of leukocytes, monocytes). One blinded investigator will evaluate all the sections. To analyze the data, we will compare histological findings between the experimental side and control.

Inductively coupled plasma atomic emission spectroscopy (ICP-AES). The tooth will be sectioned into 2 mm thick sections and dissolved in 70% nitric acid for 24 h to dissolve the hydroxyapatite and the coating of the nanoparticle. The resulting material will be filtered and run in our ICP-AES machine (Perkin Elmer Optima 4300 DV). The lower limit of quantification of iron using ICP-AES is 2 μg/2 mL. The measurements obtained from the samples will be plotted against a standard curve to quantify the amount of nanoparticles in each sample. The distribution of particles, as a function of tooth preparation parameter (for instance, dentinal depth), will then be determined.

What is claimed is:

1. A composition for treating a condition affecting a tooth or periodontium by delivery into dentinal tubules in a subject comprising biocompatible magnetic, magnetizable, or magnetically responsive agents, and an effective amount of a dental restorative/bonding material, wherein the magnetic, magnetizable, or magnetically responsive agents comprise a magnetic, magnetizable, or magnetically responsive core coated with a shell comprising a biocompatible polymer or polysaccharide matrix, wherein the magnetic, magnetizable, or magnetically responsive agents have a size of from 50 nm to 1500 nm so that they would be pulled by magnetic forces under an applied magnetic field to be delivered into the dentinal tubules of the subject, wherein the dental restorative/bonding material comprises a self-etch primer bonding agent, a self-etch adhesive bonding agent, or an etch and rinse bonding agent.

2. The composition of claim 1, wherein the dental restorative/bonding material is bound to the magnetic, magnetizable, or magnetically responsive agents chemically, ionically, covalently, non-covalently, using a thin film rehydration method, by dialysis, by mechanical absorption polymerization or a combination thereof.

3. The composition of claim 1, wherein the magnetic, magnetizable, or magnetically responsive agents have a size of from 300 nm to 1200 nm.

4. The composition of claim 1, wherein the magnetic, magnetizable, or magnetically responsive agents comprise particles, fluids, rods, cubes, liposomes or agents of other shape.

5. The composition of claim 1, wherein the magnetic, magnetizable, or magnetically responsive agents are paramagnetic, superparamagnetic materials, ferromagnetic or ferromagnetic materials.

6. The composition of claim 1, wherein the magnetic, magnetizable, or magnetically responsive agents are nanoparticles and comprise an iron core.

7. The composition of claim 6, wherein the nanoparticles are superparamagnetic iron oxide nanoparticles.

8. The composition of claim 1, wherein the magnetic, magnetizable, or magnetically responsive agents have a size of from 100 nm to 300 nm.

9. The composition of claim 1, wherein the core is coated with a biocompatible polymer.

* * * * *